US011028426B2

(12) United States Patent
Saitou et al.

(10) Patent No.: US 11,028,426 B2
(45) Date of Patent: Jun. 8, 2021

(54) NUCLEIC ACID SEQUENCE AMPLIFICATION METHOD

(71) Applicant: KYOTO UNIVERSITY, Kyoto (JP)

(72) Inventors: Mitinori Saitou, Kyoto (JP); Tomonori Nakamura, Kyoto (JP); Yukihiro Yabuta, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 15/553,091

(22) PCT Filed: Feb. 23, 2016

(86) PCT No.: PCT/JP2016/055314
§ 371 (c)(1),
(2) Date: Aug. 23, 2017

(87) PCT Pub. No.: WO2016/136766
PCT Pub. Date: Sep. 1, 2016

(65) Prior Publication Data
US 2018/0044714 A1 Feb. 15, 2018

(30) Foreign Application Priority Data

Feb. 23, 2015 (JP) .............................. JP2015-033432

(51) Int. Cl.
*C12Q 1/68* (2018.01)
*C12Q 1/6806* (2018.01)
*C12Q 1/686* (2018.01)
*C12Q 1/6851* (2018.01)
*C12Q 1/6874* (2018.01)

(52) U.S. Cl.
CPC ............. *C12Q 1/6806* (2013.01); *C12Q 1/68* (2013.01); *C12Q 1/686* (2013.01); *C12Q 1/6851* (2013.01); *C12Q 1/6874* (2013.01)

(58) Field of Classification Search
CPC ........ C12Q 1/6806; C12Q 1/68; C12Q 1/686; C12Q 1/6851
See application file for complete search history.

(56) References Cited

U.S. PATENT DOCUMENTS

| 6,271,002 B1 * | 8/2001 | Linsley | .............. | C12N 15/1096 435/4 |
| 2009/0291852 A1 * | 11/2009 | Saitou | .................... | C12Q 1/686 506/7 |

OTHER PUBLICATIONS

Kurimoto, Kazuki, et al. "Global single-cell cDNA amplification to provide a template for representative high-density oligonucleotide microarray analysis." Nature protocols 2.3 (2007): 739. (Year: 2007).*
Sasagawa et al. (Genome biology14.4 (2013): 3097). (Year: 2013).*
Sasagawa 2013 supp (Year: 2013).*
Nakamura, Tomonori, et al. "SC3-seq: a method for highly parallel and quantitative measurement of single-cell gene expression." Nucleic acids research 43.9 (2015): e60-e60; 17 pages; published online Feb. 26, 2015 (Year: 2015).*
Beck et al., "3'—End Sequencing for Expression Quantification (3SEQ) from Archival Tumor Samples," *PLoS One*, 5(1): e8768 (2010).
Grün et al., "Validation of noise models for single-cell transcriptomics," *Nat. Methods*, 11(6): 637-640 (2014).
Hashimshony et al., "CEL-Seq: Single-Cell RNA-Seq by Multi-plexed Linear Amplification," *Cell Rep.*, 2(3): 666-673 (2012).
Islam et al., "Characterization of the single-cell transcriptional landscape by highly multiplex RNA-seq," *Genome Res.*, 21(7): 1160-1167 (2011).
Islam et al., "Quantitative single-cell RNA-seq with unique molecular identifiers," *Nat. Methods*, 11(2): 163-166 and Supplemental Information (2014).
Jaitin et al., "Massively Parallel Single-Cell RNA-Seq for Marker-Free Decomposition of Tissues into Cell Types," *Science*, 343(6172): 776-779 (2014).
Kivioja et al., "Counting absolute numbers of molecules using unique molecular identifiers," *Nat. Methods*, 9(1): 72-74 (2012).
Liang et al., "Single-Cell Sequencing Technologies: Current and Future," *J. Genet. Genomics*, 41(10): 513-528 (2014).
Nakamura et al., "SC3-seq: a method for highly parallel and quantitative measurement of single-cell gene expression," *Nucleic Acids Res.*, 43(9): e60 (2015).
Picelli et al., "Smart-seq2 for sensitive full-length transcriptome profiling in single cells," *Nat. Methods*, 10(11): 1096-1098 (2013).
Ramsköld et al., "Full-Length mRNA-Seq from single cell levels of RNA and individual circulating tumor cells," *Nat. Biotechnol.*, 30(8): 777-782 (2012).
Sasagawa et al., "Quartz-Seq: a highly reproducible and sensitive single-cell RNA sequencing method, reveals non-genetic gene-expression heterogeneity," *Genome Biol.*, 14(4): R31 (2013).
Streets et al., "Microfluidic single-cell whole-transcriptome sequencing," *Proc. Natl. Acad. Sci. U.S.A.*, 111(19): 7048-7053 (2014).
Tang et al., "mRNA-Seq whole-transcriptome analysis of a single cell," *Nat. Methods*, 6(5): 377-382 (2009).

(Continued)

*Primary Examiner* — Sahana S Kaup
(74) *Attorney, Agent, or Firm* — Leydig, Voit & Mayer, Ltd.

(57) ABSTRACT

The invention provides a method of preparing a nucleic acid population suitable for RNA sequencing. The method involves amplifying a double-stranded DNA and a poly T sequence by using the DNA constituted of any additional nucleic acid sequence X, poly T sequence, mRNA sequence isolated from a biological sample, poly A sequence and any additional nucleic acid sequence Y in this order as a template, a first primer containing any additional nucleic acid sequence X having amine added to the 5'-terminal (and a poly T sequence), and a second primer containing any additional nucleic acid sequence Y (and a poly T sequence), followed by fractionalizing the DNA, phosphorylating the DNA, preparing cDNA by using the DNA as a template and a third primer, adding adenine (A) to the cDNA, linking a DNA, and amplifying the DNA by using the DNA as a template, a fourth primer, and a fifth primer.

12 Claims, 15 Drawing Sheets

(56) References Cited

OTHER PUBLICATIONS

Tang et al., "RNA-Seq analysis to capture the transcriptome landscape of a single cell," *Nat. Protoc.*, 5(3): 516-535 (2010).
Japanese Patent Office, International Search Report in International Patent Application No. PCT/JP2016/055314 (dated May 31, 2016).
Nakamura et al., "SC3-seq: a method for highly parallel and quantitative measurement of single-cell gene expression," *Nucleic Acids Res.*, 43(9): e60 and Supplementary Materials (2015).

\* cited by examiner

NUCLEIC ACID SEQUENCE AMPLIFICATION METHOD

CROSS-REFERENCE TO RELATED APPLICATIONS

This patent application is the U.S. national phase of International Patent Application No. PCT/JP2016/055314, filed on Feb. 23, 2016, which claims the benefit of Japanese Patent Application No. 2015-033432, filed Feb. 23, 2015, the disclosures of which are incorporated herein by reference in their entireties for all purposes.

TECHNICAL FIELD

The present invention relates to a method of amplifying a nucleic acid sequence for producing a sample for quantifying mRNA by using a next-generation sequencer, and particularly to an amplification method of a nucleic acid sequence which enables quantitative analysis of mRNA by using a next-generation sequencer and a small number of cells, preferably at a single cell level.

BACKGROUND ART

Quantitative transcriptome analysis of a single cell is an important tool for embryology, stem cell and cancer research. This analysis of single cell requires amplification of cDNA produced by reverse transcription of mRNA in the single cell, and two methods have been proposed as the amplification method. One is an amplification method by PCR and the other is an amplification method by T7 RNA polymerase. PCR is highly useful for transcriptome analysis of a single cell, since it shows high amplification efficiency, is convenient and has high stability.

To confirm quantitative amplification of cDNA from a single cell, a method including synthesizing a long first cDNA and analyzing the amplification product by RNA sequencing (RNA-seq) has been proposed as a method for comprehensively analyzing amplified cDNA (non-patent documents 1-3). In another method, an amplification method of cDNA from a single cell uses, for RNA-seq, a full-length cDNA amplified by a method called a template switching method (non-patent documents 4 and 5). For absolute quantification of a transcription product, unique molecular identification (UMI) is performed by attaching a tag to the 5'-side or 3'-side of the first cDNA, and the like (non-patent documents 6-10). Besides these, an analysis method by recognizing respective cells by a barcode sequence and a method including capturing a single cell by microchannel and the like have been proposed (non-patent documents 11 and 12).

While methods using RNA-seq have been proposed, reproducibility and precision of quantification have been questioned. That is, RNA-seq often accompanies PCR amplification as mentioned above; however, since amplification rate of PCR is not 100%, particularly when a small number of copies are used for amplification, reproducibility of the copy number after amplification is poor. To analyze cDNA derived from a single cell, moreover, many samples need to be analyzed. Analysis of many cells by an existing method is difficult since the unit cost of analysis per cell is high.

DOCUMENT LIST

Non-Patent Documents non-patent document 1: Tang, F., et al., Nat Methods, 6, 377-382, 2009 non-patent document 2: Tang, F., et al., Nature protocols, 5, 516-535, 2010 non-patent document 3: Sasagawa, Y., et al., Genome Biol, 14, R31, 2013 non-patent document 4: Ramskold, D., et al., Nat Biotechnol, 30, 777-782, 2012 non-patent document 5: Picelli, S., et al., Nat Methods, 10, 1096-1098, 2013 non-patent document 6: Islam, S., et al., Genome Res, 21, 1160-1167, 2011 non-patent document 7: Kivioja, T., et al., Nat Methods, 9, 72-74, 2012 non-patent document 8: Islam, S., et al., Nat Methods, 11, 163-166, 2014 non-patent document 9: Hashimshony, T., et al., Cell reports, 2, 666-673, 2012 non-patent document 10: Grun, D., et al., Nat Methods, 11, 637-640, 2014 non-patent document 11: Streets, A. M., et al., Proc Natl Acad Sci USA, 111, 7048-7053, 2014 non-patent document 12: Jaitin, D. A., et al., Science, 343, 776-779, 2014

SUMMARY OF THE INVENTION

Problems to be Solved by the Invention

Since samples obtained by existing nucleic acid sequence amplification methods target the full-length of cDNA, when the cDNA becomes long, the quantitativity of mRNA analysis using a next-generation sequencer becomes low. To simultaneously analyze many samples, moreover, an amplification method of a nucleic acid sequence for preparing samples having higher quantitativity at a low cost is desired.

Means of Solving the Problems

It is necessary to increase quantitativity of mRNA analysis using a next-generation sequencer, and decrease the unit cost of analysis. In the present invention, therefore, a sample containing only the 3' terminal side was successively obtained by the following method, by amplifying cDNA by utilizing a poly A sequence of mRNA, further fragmenting same, and selectively adding the primer sequence. As a result, an SC3-seq (Single cell mRNA 3' end sequence) method that enables simultaneous analysis of many samples with higher quantitativity has been developed.

Accordingly, the present invention relates to the following;

[1] A method of preparing a nucleic acid population comprising an amplification product maintaining a relative relationship of gene expression level in a biological sample, which method comprising (a) a step of amplifying a double-stranded DNA by using the double-stranded DNA constituted of any additional nucleic acid sequence X, poly T sequence, mRNA sequence isolated from a biological sample, poly A sequence and any additional nucleic acid sequence Y in this order as a template, a first primer comprising any additional nucleic acid sequence X having amine added to the 5'-terminal, and optionally further comprising a poly T sequence at the downstream thereof, and a second primer comprising any additional nucleic acid sequence Y, and optionally further comprising a poly T sequence at the downstream thereof, (b) a step of fractionalizing the double-stranded DNA obtained in the aforementioned step (a), (c) a step of phosphorylating the 5'-terminal of the fragmented double-stranded DNA obtained in the aforementioned step (b), (d) a step of preparing cDNA by using the double-stranded DNA obtained in the aforementioned step (c) and having a phosphorylated 5'-terminal as a template, and a third primer comprising any additional nucleic acid sequence Z and the aforementioned additional nucleic acid sequence Y in this order, and optionally further comprising a poly T sequence at the downstream thereof, and adding adenine (A) to the 3'-terminal of the cDNA, (e) a step of linking a double-stranded DNA containing any sequence V having 3'-overhang thymine (T) to the double-stranded DNA obtained in the aforementioned step (d), and (f) a step of amplifying the double-stranded DNA by using the double-stranded DNA obtained in the aforementioned step (e) as a template, a fourth primer comprising the aforementioned sequence V, and a fifth primer comprising the aforementioned additional nucleic acid sequence Z, and optionally further comprising the aforementioned additional nucleic acid sequence Y at the downstream thereof.

[2] The method of [1], wherein the double-stranded DNA constituted of any additional nucleic acid sequence X, poly T sequence, mRNA sequence isolated from a biological sample, poly A sequence and any additional nucleic acid sequence Y in this order used in the aforementioned step (a) is prepared by a method containing the following steps:

(i) a step of preparing a primary stranded cDNA by reverse transcription using an mRNA isolated from a biological sample as a template, and a sixth primer composed of the aforementioned additional nucleic acid sequence Y and the poly T sequence, (ii) a step of preparing a double-stranded DNA, which is a secondary strand, including subjecting the primary stranded cDNA obtained in step (i) to a poly A tailing reaction, and using said primary stranded cDNA as a template, and a seventh primer composed of the aforementioned additional nucleic acid sequence X and the poly T sequence, and (iii) a step of amplifying the double-stranded DNA obtained in step (ii) by using an eighth primer comprising the aforementioned additional nucleic acid sequence X, and optionally further comprising a poly T sequence at the downstream thereof, and a ninth primer comprising the aforementioned additional nucleic acid sequence Y, and optionally further comprising a poly T sequence at the downstream thereof.

[3] The method of any one of [1] or [2], wherein the fragmentation in the aforementioned step (b) is performed by sonication.

[4] The method of any one of [1] to [3], wherein smoothing of the terminal is performed simultaneously with phosphorylation of the 5'-terminal in the aforementioned step (c).

[5] The method of any one of [1] to [4], wherein the aforementioned step (c) further comprises a step of selecting a fragmented double-stranded DNA with a size of 200 bases to 250 bases, or 300 bases to 350 bases.

[6] The method of any one of [1] to [5], wherein the amplification in the aforementioned step (a) is performed by 2 to 8 cycles of PCR.

[7] The method of any one of [1] to [6], wherein the amplification in the aforementioned step (f) is performed by 5 to 20 cycles of PCR.

[8] The method of any one of [2] to [7], wherein the amplification in the aforementioned step (iii) is performed by 5 to 30 cycles of PCR.

[9] The method of any one of [1] to [8], wherein the fifth primer used in the aforementioned step (f) further comprises a barcode sequence.

[10] The method of any one of [1] to [9], wherein the biological sample is one to several cells.

[11] The method of [10], wherein the biological sample is one cell.

[12] A method of measuring an amount of mRNA in cells for preparing a nucleic acid population, comprising measuring, by a next-generation sequencer, the amount of the aforementioned amplified double-stranded DNA in the nucleic acid population prepared by the method of [1] to [11].

[13] A kit for preparing a cDNA population to be applied for the measurement of mRNA amount by a next-generation sequencer, which comprises the following:

(a) the first primer comprising any additional nucleic acid sequence X having amine added to the 5'-terminal, and optionally further comprising a poly T sequence at the downstream thereof (b) the second primer comprising any additional nucleic acid sequence Y, and optionally further comprising a poly T sequence at the downstream thereof (c) the third primer comprising any additional nucleic acid sequence Z and the aforementioned additional nucleic acid sequence Y in this order, and optionally further comprising a poly T sequence at the downstream thereof (d) a double-stranded DNA comprising any sequence V having 3'-overhang thymine (T)

(e) the fourth primer comprising the aforementioned sequence V (f) the fifth primer comprising the aforementioned additional nucleic acid sequence Z, and optionally further comprising the aforementioned additional nucleic acid sequence Y at the downstream thereof.

[14] The kit of [13], wherein the fifth primer in the aforementioned (f) further comprises a barcode sequence.

[15] The kit of [13] or [14], further comprising (g) the sixth primer consisting of the aforementioned additional nucleic acid sequence Y and poly T sequence, (h) the seventh primer consisting of the aforementioned additional nucleic acid sequence X and poly T sequence, (i) the eighth primer comprising the aforementioned additional nucleic acid sequence X, and optionally further comprising a poly T sequence at the downstream thereof, and (j) the ninth primer comprising the aforementioned additional nucleic acid sequence Y, and optionally further comprising a poly T sequence at the downstream thereof.

[16] The kit of [15], wherein the aforementioned sixth primer and the aforementioned ninth primer are the same, and/or the aforementioned seventh primer and the aforementioned eighth primer are the same.

[17] The kit of [15] or [16], wherein the aforementioned second primer and the aforementioned ninth primer are the same.

[18] The kit of any one of [13] to [17], further comprising polymerase used for DNA amplification.

Effect of the Invention

The present invention provides a quantitative amplification technique of an extremely small quantity of cDNA by a convenient PCR method, which is directly applicable to oligonucleotide microarray and is highly reliable. In the method of the present invention, template cDNA in an amount sufficient for a microarray experiment can be synthesized and amplified from a single cell by a one-day experiment. The conventional method and the method of the present invention are compared by a real-time PCR experiment using some gene products as probes, and it was confirmed that both systematic error (lineage error) and random error were markedly improved without doubt. Furthermore, in a transcriptome analysis experiment using the method of the present invention, it was confirmed that quantitative analysis at a single cell level with good reproducibility, which is far improved than a conventional method, has become possible.

Figure 1:
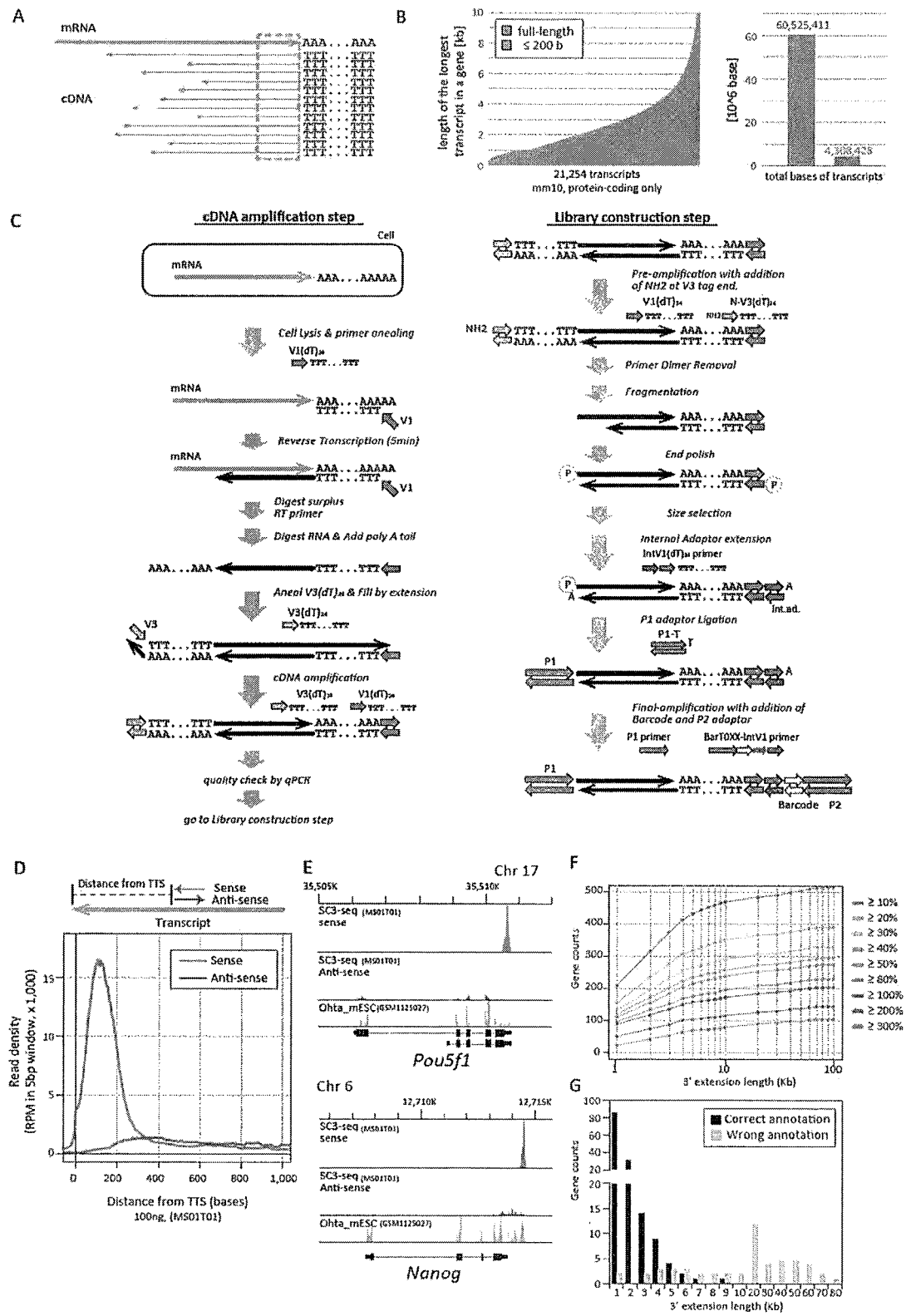
FIG. 1A shows the concept of the SC3-seq. The SC3-seq targets only the 3' ends shown with orange dotted square in the Figure.
FIG. 1B is a graph showing 21,254 protein-coding genes annotated in the Mouse mm10 database, which are aligned in the order of the length of their transcripts (left). In the right Figure, while the sum of all the lengths of the transcripts is around 60 Mbp, that of the 200 bp from the 3' ends of all transcripts is only 4 Mbp.
FIG. 1C shows the scheme for the SC3-seq. The left Figure shows the cDNA synthesis and amplification steps, and the right shows library construction steps.
FIG. 1D is a graph showing the averaged SC3-seq track [read density (RPM, ×1000 reads) plotted against the read position from the annotated TTSs] of 100 ng of RNAs from mESCs. In the Figure, the red line represents the track of reads mapped on the sense strands; and the blue line shows the track of reads mapped on the anti-sense strands.
FIG. 1E shows the positions of the SC3-seq reads of the Pou5f1 and Nanog loci. The red peaks indicate the reads mapped on the sense strands, and the blue peaks show the reads mapped on the anti-sense strands.
FIG. 1F is a graph plotting gene counts against the extent of the definition of the 3' end extension. The gene counts show an increase in the number of reads as indicated by the color codes.
FIG. 1G is a graph showing gene counts for correct (black bars) or wrong annotations by the extension of the definition of the TTSs by the indicated length. The 205 genes that exhibited gene counts of not less than 2-fold (×2, ×3, ×4 in FIG. 1F) by extending the definition of the TTSs by 10 Kb were visually inspected for collect/wrong annotations in comparison to the published RNA-seq data.

DESCRIPTION OF EMBODIMENTS (1) Method of Preparing Nucleic Acid Population Composed of Amplification Product Maintaining Relative Relationship of Gene Expression Level in Biological Sample The present invention provides a method of preparing a nucleic acid population containing an amplification product maintaining a relative relationship of gene expression level in a biological sample, and a nucleic acid population obtained by the method.

In the present invention, the "amplification product maintaining a relative relationship of gene expression level in a biological sample" means an amplification product (group) mostly maintaining the constitution of the gene product group as a whole (quantitative ratio between respective gene products) in a biological sample, and an amplification product (group) ensuring a level permitting application of the standard protocol for quantifying mRNA by a next-generation sequencer.

In the present invention, the "biological sample" means eukaryotic cells of a species having poly A at the 3'-terminal of mRNA, for example, animals including mammals such as human, mouse, Macaca fascicularis and the like, plant, fungus, protist and the like. The present invention is particularly expected as a biological sample applicable to the cells contained in embryo in the developmental process, and pluripotent stem cell having versatility.

While the number of cells as a biological sample is not particularly limited, considering that the cells can be amplified with good reproducibility while maintaining the relative relationship of gene expression level in biological samples in the present invention, the applicable number of cells is of the level of not more than 100, several tens, one to several, ultimately one.

"Quantitation of mRNA by next-generation sequencer" means RNA sequencing (also referred to as RNA-Seq), and means counting of mRNA having the sequence, along with sequencing of the mRNA, namely, quantifying. As a next-generation sequencer to be used for such object, one commercially available from Illumina, Life Technologies, or Roche Diagnostic can be used.

The method of the present invention includes the following steps:
(a) a step of amplifying the double-stranded DNA by using a double-stranded DNA constituted of any additional nucleic acid sequence X, poly T sequence, mRNA sequence (actually cDNA sequence corresponding to mRNA sequence (hereinafter the same)) isolated from a biological sample, poly A sequence and any additional nucleic acid sequence Y in this order as a template, a first primer comprising any additional nucleic acid sequence X having amine added to the 5'-terminal, and a second primer comprising any additional nucleic acid sequence Y,
(b) a step of fractionalizing the double-stranded DNA obtained in the aforementioned step (a),
(c) a step of phosphorylating the 5'-terminal of the fragmented double-stranded DNA obtained in the aforementioned step (b),
(d) a step of preparing cDNA by using the double-stranded DNA obtained in the aforementioned step (c) and having a phosphorylated 5'-terminal as a template, and a third primer comprising any additional nucleic acid sequence Z and the aforementioned additional nucleic acid sequence Y in this order, and adding adenine (A) to the 3'-terminal of the cDNA,
(e) a step of linking a double-stranded DNA containing any sequence having 3'-overhang thymine (T) to the double-stranded DNA obtained in the aforementioned step (d), and
(f) a step of amplifying the double-stranded DNA by using the double-stranded DNA obtained in the aforementioned step (e) as a template, a fourth primer comprising any sequence V, and a fifth primer comprising the aforementioned additional nucleic acid sequence Z.

Figure 14:
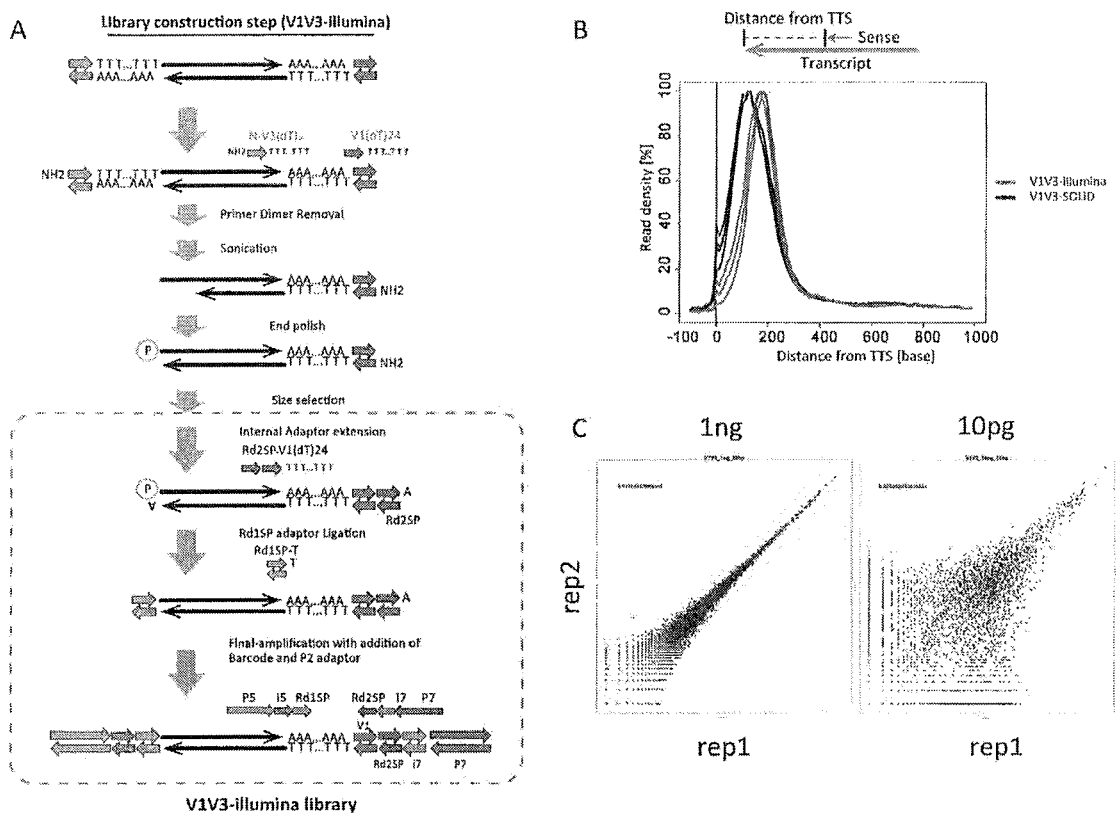
FIG. 14A shows an outline of the construction of a library corresponding to the next-generation sequencer (Miseq, Nextseq500, Hiseq2000/2500/3000/4000) of Illumina. The difference from the aforementioned library for SOLiD5500xl is the use of the DNA sequence (red broken line) specified by Illumine as the tag.
FIG. 14B shows a graph plotting, in 1 ng of RNA extracted from mESC, average SC3-seq track (read density (RPM, ×1,000 reads) against the position of read from the annotated TTS (transcription termination site).
FIG. 14C is a scatter diagram showing comparison of two independent replicates amplified from 1 ng and 10 pg of total RNA of mESC based on the analysis by Miseq of Illumina.
Figure 15:
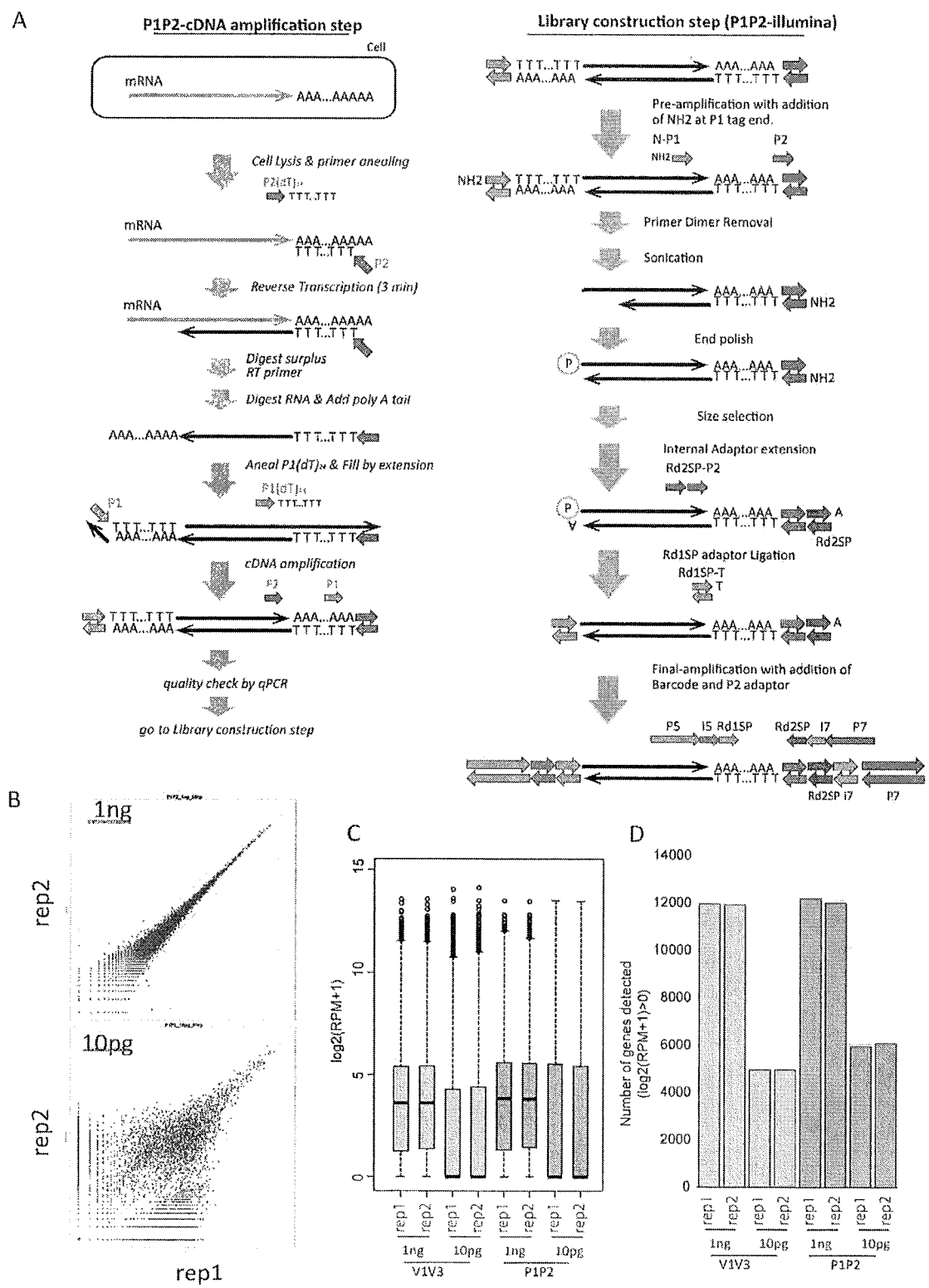
FIG. 15A shows the outline of the SC3-seq method for the analysis by changing the aforementioned V1V3 to a novel DNA sequence P1P2 and using the next-generation sequencer (Miseq, Nextseq500, Hiseq2000/2500/3000/4000) of Illumina.
FIG. 15B is a scatter diagram showing comparison of two independent replicates amplified from 1 ng and 10 pg of total RNA of mESC by utilizing the P1P2 tag and based on the analysis by Miseq of Illumina.
FIG. 15C, D show a box plot of the distribution of the expression level of all genes obtained by analyzing, by Miseq of Illumina, cDNA amplified from 1 ng and 10 pg RNA by using V1V3 tag and P1P2 tag, respectively (C), and the number of detected genes shown in a bar graph (D).

An outline of the method of the present invention is shown in FIG. 1C, FIG. 14A and FIG. 15A. These figures merely explain one embodiment of the method of the present invention, and those of ordinary skill in the art can appropriately modify and perform the present invention. In the following, each step of the method of the present invention is explained in detail by referring to FIG. 1C and FIG. 15A.
(a) step of amplifying the double-stranded DNA by using a double-stranded DNA constituted of any additional nucleic acid sequence X, poly T sequence, mRNA sequence isolated from a biological sample, poly A sequence and any additional nucleic acid sequence Y in this order as a template, a first primer comprising any additional nucleic acid sequence X having amine added to the 5'-terminal, and a second primer comprising any additional nucleic acid sequence Y The double-stranded DNA constituted of any additional nucleic acid sequence X, poly T sequence, mRNA sequence isolated from a biological sample, poly A sequence and any additional nucleic acid sequence Y in this order to be used in this step can be prepared by the following steps (i) to (iii) (see WO 2006/085616 for reference).
(i) Preparation of Primary Stranded cDNA
Primary stranded cDNA is prepared reverse transcription using an mRNA isolated from a biological sample as a template, and the sixth primer composed of the aforementioned additional nucleic acid sequence Y and a poly T sequence.

The time of the reverse transcription reaction is preferably shortened to 5-10 min, more preferably about 5 min, to prevent the amplification efficiency in the subsequent PCR reaction from depending on the length of the template cDNA. In this way, primary stranded cDNAs having the same length can be synthesized for mRNA having a long full-length. An "almost uniform length of primary stranded cDNAs" means that primary stranded cDNAs with the same length can be obtained for such mRNA having a long full-length, and does not exclude the presence of a shorter cDNA.

It is desirable to remove the sixth primer remaining after this preparation by decomposition or other method. Typically, the remaining primer can be decomposed by exonuclease I or exonuclease T. Alternatively, it can also be deactivated by modifying the 3'-side of the remaining primer with alkaline phosphatase and the like.
(ii) Preparation Step of Secondary Stranded (Double-Stranded) cDNA by Using Poly A Tailing Reaction and the Seventh Primer The primary stranded cDNA obtained in step (i) is subjected to a poly A tailing reaction, and a double-stranded DNA which is a secondary strand is obtained using the primary stranded cDNA as a template and the seventh primer composed of the aforementioned additional nucleic acid sequence X and the poly T sequence.

The first primer used here and the second primer used in step (i) are characterized in that they have mutually different nucleic acid sequences but have constant identity and are free of a promoter sequence.

The sixth and seventh primers are explained in more detail below.

The additional nucleic acid sequences X and Y in the sixth primer used in step (i): additional nucleic acid sequence Y and poly T sequence, and the seventh primer used in step (ii): additional nucleic acid sequence X and poly T sequence have sequences different from each other. By using different primers at the 3'-side and the 5'-side of cDNA, the directivity for distinguishing the 3'-side and the 5'-side in the subsequent PCR amplification can be imparted.

The common sequence of the additional nucleic acid sequences X and Y is selected such that the Tm value of the common sequence in X and Y is lower than the Tm value of each of the sixth and seventh primers, and the values are different as much as possible. In this manner, undesirable crossannealing of the sixth and seventh primers to different sites can be prevented during annealing in the subsequent PCR reaction. In other words, the Tm value of the common sequence is selected not to exceed the annealing temperature after annealing of the sixth and seventh primers. Tm value is the temperature at which half the number of DNA molecules anneal to complementary strands. The annealing temperature is set to a temperature that enables pairing of the primers, and is generally set to a temperature lower than the Tm value of the primer.

Preferably, the nucleic acid sequences of the sixth primer and the seventh primer have not less than 77%, more preferably not less than 78%, further preferably 80±1%, most preferably 79%, of identity. The upper limit of the sequence identity is, as mentioned above, the upper limit % at which the Tm value of the common sequence of the both primers does not exceed the annealing temperature. Alternatively, the nucleic acid sequences of the sixth primer and the seventh primer can also be defined as sequences in which additional nucleic acid sequences X and Y have not less than 55%, more preferably not less than 57%, further preferably 60±2%, of identity. The upper limit of the sequence identity is the upper limit % at which the Tm value of the common sequence of the additional nucleic acid sequences X and Y does not exceed the annealing temperature in the PCR reaction.

The additional nucleic acid sequences X and Y in the sixth and seventh primers to be used each preferably have a palindromic sequence. Specifically, since almost all restriction enzyme moieties, for example, AscI, BamHI, SalI, XhoI moiety, other EcoRI, EcoRIV, NruI, NotI and the like, have a palindromic sequence, they can have these sequences. Thus, specific examples of the sixth and seventh primers include a primer set of a nucleic acid molecule having the nucleic acid sequence shown in SEQ ID NO: 1 (atatctcgagggcgcgccggatccttttttttttttttttttttttt) and a nucleic acid molecule having the nucleic acid sequence shown in SEQ ID NO: 2 (atatggatccggcgcgccgtcgactttttttttttttttttttttttt). When a next-generation sequencer of Illumina is used, the detection precision can be improved by using P2(dT)$_{24}$ sequence (SEQ ID NO: 6: ctgccccggggttcctcat-tcttttttttttttttttttttttt) as the sixth primer, and P1(dT)$_{24}$ sequence (SEQ ID NO: 7: ccactacgcctccgctttcctctc-tatggttttttttttttttttttttttt) (length of poly T sequence can be changed as appropriate) as the seventh primer.

Furthermore, the sixth and seventh primers to be used are preferably primers having higher specificity or higher Tm value than those of the primers used for general PCR. Using a primer having higher Tm value than that of the primers used for general PCR, the annealing temperature can be set closer to the Tm value of the primer, which in turn can suppress non-specific annealing.

Since the annealing temperature is typically 55° C., the Tm value used for general PCR is 60° C. Thus, the annealing temperature of the primer to be used in the present invention is not less than 60° C. and less than 90° C., preferably about 70° C., most preferably 67° C.

(iii) PCR Amplification

Then, PCR amplification is performed using the double-stranded DNA obtained in step (ii) as a template, and by adding the eighth primer containing the aforementioned additional nucleic acid sequence X, and the ninth primer containing the aforementioned additional nucleic acid sequence Y. As the eighth primer, the aforementioned seventh primer further comprising poly T sequence at the downstream of the additional nucleic acid sequence X may be used. As the ninth primer, the aforementioned sixth primer further comprising poly T sequence at the downstream of the additional nucleic acid sequence Y may also be used (FIG. 1C). When the next-generation sequencer of Illumina is used, P1 sequence (SEQ ID NO: 8: ccactacgcctccgctttcctctctatg) can be used as the eighth primer, and P2 sequence (SEQ ID NO: 10: ctgccccggggttcctcattct) can also be used as the ninth primer (FIG. 15A).

The cycles of PCR can be appropriately changed according to the amount of mRNA isolated from the biological sample to be used, i.e., the number of cells to be used. Examples thereof include 5 to 30 cycles of PCR, more preferably 7 cycles when mRNA contained in 100 ng of total RNA is used as the template. Similarly exemplified are 11 cycles when mRNA contained in 10 ng of total RNA is used as the template, 14 cycles when mRNA contained in 1 ng of total RNA is used as the template, 17 cycles when mRNA contained in 100 pg of total RNA is used as the template, and 20 cycles when mRNA contained in 10 pg of total RNA is used as the template.

In step (iii), non-specific annealing can be suppressed by setting the annealing temperature in PCR amplification closer to the Tm value of the primer to be used. For example, a primer set of a nucleic acid molecule having the nucleic acid sequence shown in SEQ ID NO: 1 and a nucleic acid molecule having the nucleic acid sequence shown in SEQ ID NO: 2 is used, the annealing temperature is not less than 60° C. and less than 90° C., preferably about 70° C., most preferably 67° C.

In step (iii), primary stranded cDNAs derived from the same starting sample are preferably divided into plural, for example, 3-10, preferably about 4, tubes, each of which is subjected to PCR reaction, and they are finally mixed. In this way, random errors are averaged and can be markedly suppressed.

The double-stranded DNAs amplified in step (iii) are coamplified using, for example, ERCC spike-in RNA commercially available from Life Technologies as a template, the amounts and assumed copy numbers thereof are compared, and whether the amplification by the aforementioned PCR was performed normally can be confirmed.

In step (a), using a double-stranded DNA obtained as mentioned above as a template, the first primer containing the aforementioned additional nucleic acid sequence X having amine added to the 5'-terminal, and the second primer comprising the aforementioned additional nucleic acid sequence Y, the double-stranded DNA is amplified, whereby amine can be added to the 5'-terminal of the additional nucleic acid sequence X in the double-stranded DNA. The first and second primers may further contain poly T sequence at the downstream of the additional nucleic acid sequences X and Y, respectively. Therefore, the seventh primer having amine added to the 5'-terminal used in step (ii) can be used as the first primer, and the sixth primer used in step (i) can be used as the second primer (FIG. 1C). Alternatively, when primers free of poly T sequence are used as the eighth and ninth primers in step (iii), the eighth primer having amine added to the 5'-terminal can also be used as the first primer, and the ninth primer can also be used as the second primer (FIG. 15A).

By the addition of the amine, phosphorylation of the 5'-terminal side of the mRNA sequence can be suppressed in the subsequent step (c), and a library having only the 3'-terminal side of the mRNA sequence can be constructed. The amplification in step (a) is not particularly limited as long as amine can be added to the 5'-terminal of the additional nucleic acid sequence X in the double-stranded DNA. For example, it is performed by 2-8 cycles, preferably 4 cycles, of PCR. The amine to be added is not particularly limited as long as it can suppress phosphorylation of the 5'-terminal in step (c), and an amino group is preferably added.

(b) step of fractionalizing the double-stranded DNA obtained in the aforementioned step (a)

In step (b), the double-stranded DNA obtained in step (a) is fractionalized. For fragmentation of DNA, for example, a division method using ultrasonication or a method using DNA fragmentating enzyme is available. In the present invention, a division method using ultrasonication is preferably used.

(c) step of phosphorylating the 5'-terminal of the fragmented double-stranded DNA obtained in the aforementioned step (b)

In step (c), the 5'-terminal of the fragmented double-stranded DNA obtained in step (b) is phosphorylated. The phosphorylation can be performed using a nucleic acid kinase known per se. However, as mentioned above, a 5'-terminal added with amine cannot be phosphorylated. When fragmentation is performed by ultrasonication in step (b), the cleaved terminal may not be smoothed. Thus, it is desirable to smooth the terminal by using DNA polymerase, and then perform step (c).

After step (c), a step for selecting a fragmented double-stranded DNA having any base length may be performed. While the base length is not particularly limited as long as mRNA can be recognized by sequencing, it is preferably 200 to 250 base length by SOLiD5500xl of Life Technologies, and 350 to 500 base length by Miseq/NextSeq500/Hiseq2000/2500/3000/4000 of Illumina.

The step for selecting DNA may be performed by any means known in the field such as DNA adsorption method, gel filtration method, gel electrophoresis and the like. The step can be conveniently performed using AMPureXP beads of Beckman Coulter.

(d) step of preparing cDNA by using the double-stranded DNA obtained in the aforementioned step (c) and having a phosphorylated 5'-terminal as a template, and a third primer comprising any additional nucleic acid sequence Z and the aforementioned additional nucleic acid sequence Y in this order, and adding adenine (A) to the 3'-terminal thereof In step (d), using the double-stranded DNA having the phosphorylated 5'-terminal, which is obtained in step (c), as a template, and the third primer which is the second primer comprising the aforementioned additional nucleic acid sequence Y (and optionally further comprising poly T sequence) further having any additional nucleic acid sequence Z at the 5'-side, the additional nucleic acid sequence Z is added to the 5'-terminal of the phosphorylated double-stranded DNA. In this step, additional nucleic acid sequence Z can be added to the additional nucleic acid sequence Y in the double-stranded DNA by elongation reaction using the double-stranded DNA having the phosphorylated 5'-terminal, which is obtained in step (c), as a template, the third primer added thereto, and DNA polymerase. By using, as DNA polymerase, an enzyme having a TdT activity to add adenine (A) to the 3'-terminal, adenine (A) is added to the 3'-terminal of each strand of the double-stranded DNA. By this step (d), a double-stranded DNA constituted of mRNA sequence having phosphorylated 5'-terminal and isolated from a biological sample, poly A sequence, any additional nucleic acid sequence Y and any additional nucleic acid sequence Z in this order can be obtained. The optional additional nucleic acid sequence Z is a sequence relying on the next-generation sequencer to be used, and a sequence recommended by the manufacturer of the sequencer can be used. For example, when SOLiD5500XL of Life Technologies is used, any sequence shown in SEQ ID NO: 3 (ctgctgtacggccaaggcgt) can be used as additional nucleic acid sequence Z. When Miseq/NextSeq500/Hiseq2000/2500/3000/4000 of Illumina is used, Rd2SP sequence shown in SEQ ID NO: 13 (gtgactggagttcagacgtgtgctcttccgatc) can be used as the additional nucleic acid sequence Z.

(e) step of linking a double-stranded DNA containing any sequence having 3'-overhang thymine (T) to the double-stranded DNA obtained in the aforementioned step (d)

The double-stranded DNA containing any sequence V having thymine (T) overhang at the 3'-terminal of sense strand (double-stranded DNA obtained in step (d) and containing a strand linked to strand containing sense strand of mRNA sequence) is a double-stranded DNA in which only one base (T) lacks a complementary chain at the 3'-terminal side, and when the overhang has, at the 5'-terminal of the double-stranded DNA to be linked, a complementary strand which is similarly a one base (A) overhang, ligation at the protruding terminal becomes possible. In the present invention, sequence V is a sequence relying on the next-generation sequencer to be used and, for example, a sequence commercially available from Life Technologies and Illumina can be employed. Specifically, for example, P1-T (SEQ ID NO: 11: ccactacgcctccgctttcctctctatgt) in FIG. 1C, and Rd1SP-T (SEQ ID NO: 12: tctttccctacacgacgctcttccgatct) (both sense strands) in FIG. 15A can be used.

(f) step of amplification by using the double-stranded DNA obtained in the aforementioned step (e) as a template, a fourth primer comprising the aforementioned sequence V, and a fifth primer comprising the aforementioned additional nucleic acid sequence Z.

In step (f), the fourth and fifth primers to be used are sequences relying on the next-generation sequencer to be used. The fifth primer only needs to contain at least additional nucleic acid sequence Z, and may further contain the aforementioned additional nucleic acid sequence Y at the downstream thereof. More preferably, the fifth primer desirably further comprises a barcode sequence, and desirably further contains an adapter sequence having any sequence. For example, as the fourth and fifth primers, sequences commercially available from Life Technologies and Illumina can be used.

In step (f), the number of cycles of amplification is not particularly limited as long as double-stranded DNA not amplified by the fourth and fifth primers (fragmented double-stranded DNA containing 3'-terminal side or internal sequence of mRNA sequence) decreases relatively. It is, for example, 5 to 30 cycles, preferably 9 cycles, of PCR amplification.

The nucleic acid population in the present invention obtained by the above-mentioned step is useful as a sample to be applied to a next-generation sequencer and used for the sequencing and the measurement of the nucleic acid number. Particularly, since only the 3'-side is specifically extracted, a library certainly containing a part of mRNA can be constructed. Therefore, it is superior in the quantification of amplified mRNA, and can detect expression levels of mRNA more accurately and comprehensively as compared to conventional RNA-Seq.

In another embodiment, the present invention provides a kit for preparing a cDNA population to be applied to the measurement of mRNA amount by a next-generation sequencer.

The kit of the present invention may be constituted of the following primers mentioned above:

(a) the first primer comprising any additional nucleic acid sequence X having amine added to the 5'-terminal (and optionally further comprising a poly T sequence)

(b) the second primer comprising any additional nucleic acid sequence Y (and optionally further comprising a poly T sequence)

(c) the third primer comprising any additional nucleic acid sequence Z and the aforementioned additional nucleic acid sequence Y in this order (and optionally further comprising a poly T sequence)

(d) a double-stranded DNA comprising any sequence V having 3'-overhang thymine (T)

(e) the fourth primer comprising the aforementioned sequence V, and (f) the fifth primer comprising the aforementioned additional nucleic acid sequence Z (and optionally further comprising the aforementioned additional nucleic acid sequence Y).

The kit may further contain the following primer sets for preparing a double-stranded DNA constituted of any additional nucleic acid sequence X, poly T sequence, mRNA sequence isolated from a biological sample, poly A sequence and any additional nucleic acid sequence Y in this order:
(g) the sixth primer consisting of the aforementioned additional nucleic acid sequence Y and poly T sequence,
(h) the seventh primer consisting of the aforementioned additional nucleic acid sequence X and poly T sequence,
(i) the eighth primer comprising the aforementioned additional nucleic acid sequence X, and optionally further comprising a poly T sequence at the downstream thereof, and
(j) the ninth primer comprising the aforementioned additional nucleic acid sequence Y, and optionally further comprising a poly T sequence at the downstream thereof.
As used herein, the aforementioned sixth primer and the aforementioned ninth primer may be the same, or the aforementioned seventh primer and the aforementioned eighth primer may be the same. Furthermore, the aforementioned second primer and the aforementioned ninth primer may be the same.

The kit may further contain other reagents (e.g., DNA polymerase, dNTP mix, buffer etc.) necessary for PCR reaction and other reagents necessary for ligation reaction, reverse transcription reaction, terminal phosphorylation reaction and the like.

The present invention is explained in more detail in the following by referring to Examples, which are not to be construed as limitative.

EXAMPLE 1

RNA Extraction

All the animal experiments were performed under the ethical guidelines of Kyoto University. The mouse embryonic stem cell (mESC) line BVSC R8 was cultured as reported previously (Hayashi, K. et al, Cell, 146, 519-532, 2011), and total RNAs from the line were extracted using an RNeasy mini kit [Qiagen (74104)] according to the manufacturer's instructions. The extracted RNAs were serially diluted by double-distilled water (DDW) to concentrations of 250 ng/μl, 25 ng/μl, 2.5 ng/μl, 250 pg/μl and 25 pg/μl for use in evaluation of the quantitative performance of the single-cell mRNA 3-prime end sequencing (hereinafter referred to as SC3-seq).

For isolating mouse blastocysts, C57BL/6 mice were mated and noon of the day when a copulation plug was identified was designated as embryonic day (E) 0.5. At E4.5, pre-implantation blastocysts were isolated from the uteri by KSOM[Merck Millipore (MR-020P-5D)], and then they were bisected into a polar part containing an inner cell mass (ICM) and polar trophectoderm (pTE) and a mural part containing mural TE (mTE) by a glass needle under a dissection microscope [Leica Microsystems (M80)]. Each fragment was incubated with 0.25% trypsin/PBS[Sigma-Aldrich (T4799)] for around 10 min at 37° C., then dissociated into single cells by pipetting and suspended in 0.1 mg/ml of PVA/PBS [Sigma-Aldrich (P8136)] in preparation for the SC3-seq analysis.

The dealing with human samples was approved by the Ethics Committee, Graduate School of Medicine, Kyoto University, with written informed consent provided by each donor. For the analysis of human-induced pluripotent stem cells (hiPSCs), two iPSC lines, 585A1 and 585B1 (Okita, K. et al, Stem Cells, 31, 458-466, 2013), which are human iPS cells (hiPSCs), were cultured either under a conventional culture condition [DMEM/F12 [Life Technologies (11330-32)] supplemented with 20% (vol/vol) Knockout Serum Replacement [KSR; Life Technologies (10828-028)], 1% (vol/vol) GlutaMax [Life Technologies (35050-061)], 0.1 mM nonessential amino acids [Life Technologies (11140-050)], 4 ng/ml recombinant human bFGF [Wako Pure Chemical Industries (064-04541)] and 0.1 mM 2-mercaptoethanol [Sigma-Aldrich (M3148)]] on the SNL feeder cells or under a feeder-free condition (Nakagawa, M, et al, Scientific reports, 4, 3594, 2014 or Miyazaki, T. et al, Nat Commun, 3, 1236, 2012). For the isolation of hiPSCs from the feeders, the culture was first treated with CTK solutions [0.25% Trypsin [Life Technologies (15090-046)], 0.1 mg/ml Collagenase IV [Life Technologies (17104-019)], 1 mM $CaCl_2$ [Nacalai Tesque (06729-55)]] for the removal of the feeder cells, then dissociated into single cells using accutase [Innovative Cell Technologies]. For the preparation of single cells under a feeder-free system, the cells were dissociated into single cells with 0.5×TrypLE Select [TrypLE Select [Life Technologies (12563011)] diluted 1:1 with 0.5 mM EDTA/PBS]. Dissociated single state hiPSCs were transferred into 1% KSR/PBS containing 10 μM of the ROCK inhibitor Y-27632 [Wako Pure Chemical Industries (2257-00511)] in preparation for the SC3-seq analysis.

Animal experiment using cynomolgus monkeys were approved by the Animal Care and Use Committee of Shiga University of Medical Science. The procedures in cynomolgus monkeys for superovulation, oocyte collection, artificial insemination, early embryo culture, transfer of the embryos into foster mothers, and isolation of post-implantation embryos were performed as reported previously. J Yamasaki and others, 'Vitrification and Transfer of Cynomolgus Monkey (Macaca Fascicularis) Embryos Fertilized by Intracytoplasmic Sperm Injection.', Theriogenology, 76.1 (2011), 33-38 <http://dx.doi.org/10.1016/j.theriogenology.2011.01.010>.

cDNA Synthesis and Amplification for the SC3-Seq Analysis

V1V3-cDNA synthesis and amplification from isolated RNAs of single cells were performed essentially as reported previously ((Kurimoto, K. et al, Nucleic Acids Res, 34, e42, 2006 or Kurimoto, K. et al, Nature protocols, 2, 739-752, 2007), except that the Qiagen RNase inhibitor [0.4 U/sample, Qiagen (129916)], the Porcine Liver RNase inhibitor [0.4 U/sample, Takara Bio (2311A)] and the spike-in RNAs developed by the External RNA Controls Consortium [ERCC; Life Technologies (4456740)] were used, and different numbers of PCR cycles were employed for amplification depending on the amounts of total RNAs (total RNA 100 ng: 7 cycles; 10 ng: 11 cycles; 1 ng: 14 cycles; 100 pg: 17 cycles; 10 pg: 20 cycles). P1P2-cDNA synthesis and amplification are different from V1V3-cDNA synthesis and amplification in the use of SuperScript4 (Life Technologies (Ser. No. 18/090,200)) and KOD FX NEO (Toyobo (KFX-201)). A total of 62,316 or 12,463 copies of the ERCC spike-in RNAs were added to the Lysis buffer per 10 pg of total RNAs and single cells, respectively. Prior to the construction of the SC3-seq library, the quality of the amplified cDNAs was evaluated by examining the Ct values of the quantitative real-time PCR (Q-PCR) of the ERCC spike-in RNAs and several endogenous genes (see Supplementary Table S3 for the primer list), and by examining the cDNA fragment proportion by LabChip GX [Perkin Elmer] or Bioanalyzer 2100 [Agilent Technologies]. For mESC total RNA dilution analysis, ERCC-00074, 9030 copies; ERCC-00004, 4515 copies; ERCC-00113, 2257 copies; ERCC-00136, 112.8 copies; ERCC-00042, 282.2 copies; ERCC- 00095, 70.5 copies; ERCC-00019, 17.6 copies; and ERCC-00154: 4.4 copies were used, and for the analyses of mouse pre-implantation embryos and hiPSCs, ERCC-00096: 1806 copies; ERCC-00171: 451.5 copies; and ERCC-00111: 56.4 copies were used. As the endogenous genes, those described in Table 1 were used.

|  | Target | Primer set name | sense primer | anti-sense primer |
|---|---|---|---|---|
| Table 1-1 | | | | |
| ERCC spike-in | ERCC-00074 | ERCC-00074-qPCR-s1/as1 | AAGTGAGGCTCTCTCAT TGGTTT | CTGGGGTTATGAGTAG GGATGAG |
|  | ERCC-00004 | ERCC-00004-qPCR-s1/as1 | GACATCTTCATAAGGGG TTGGGT | GGCAAGCCGGTGATTT TATCTAC |
|  | ERCC-00113 | ERCC-00113-qPCR-s1/as1 | TACCCTGTAGAACCCGA CTTTTG | TTAAGCTCTGCACCTGT TACACT |
|  | ERCC-00136 | ERCC-00136-qPCR-s1/as1 | GATGTTTGGACTGATGG AAGCAC | GATTTCAGCATGTTGAG CTTCGT |
|  | ERCC-00042 | ERCC-00042-qPCR-s1/as1 | GTGGTCTGCATAAGGGT AGAGAG | GCTTTGTCTTTAAACGC TCACCT |
|  | ERCC-00095 | ERCC-00095-qPCR-s1/as1 | ATCCGTCAATAAAACCT CTGGCT | GGCTTTGTGGGATGAG GTTAAAG |
|  | ERCC-00019 | ERCC-00019-qPCR-s1/as1 | TCTGTCTGTTAGTGAGA GCCCTA | TTTTGACCTAGCCCCAT CTACAC |
|  | ERCC-00154 | ERCC-00154-qPCR-s1/as1 | CACGCGCTATTCAGACG TTATTT | TGGATATCCTCGCTTGA GTTGAC |
|  | ERCC-00096 | ERCC-00096-qPCR-s1/as1 | GATCCCGGAAGATACGC TCTAAG | CGCAGGTTGATGCTTCC AATAAA |
|  | ERCC-00171 | ERCC-00171-qPCR-s1/as1 | CAGGCAAGAGTTCAATC GCTTAG | TAGCCTTCAGTGACTGT GAGATG |
|  | ERCC-00111 | ERCC-00111-qPCR-s1/as1 | CCAACCCCACATTGTAA CTTCG | GTCTTTACTTACGCGCT CCTCT |
| Mouse | Cdx2 | Cdx2(+)/(-) | ATTGTTTGCTGCTGTTC GAGTC | CGACTTCCCTTCACCAT ACAAC |
|  | Dnmt3a | Dnmt3a-2(+)/(-) | GACTCGCGTGCAATAAC CTTAG | GGTCACTTTCCCTCACT CTGG |
|  | Dnmt3b | Dnmt3b(+)/(-) | CTCGCAAGGTGTGGGCT TTTGTAAC | CTGGGCATCTGTCATCT TTGCACC |
|  | Dppa2/ECAT15-2 | musDppa2-qPCR-s1/as1 | CATGTAGCAACTCCAGT GGACC | ACATCAGTACTGGCTAA GTGGT |
|  | Dppa3/Stella | Stella-B(+)/(-) | AGGCTCGAAGGAAATG AGTTTG | TCCTAATTCTTCCCGATT TTCG |
| Table 1-2 | | | | |
|  | Dppa4/ECAT15-1 | musDppa4-qPCR-s1/as1 | GTTTTGCTGCAAGTAG GTCCTG | GACTGCTGAACTGGTT ATGACG |
|  | Dppa5/Esg1 | Qesg1-5/3 | AAGGAGTGCTGAAGCT GGAGG | CAGCTTAACCTGCATC CAGGTC |
|  | Esrrb | musEsrrb-qPCR-s1/as1 | GCCTTTACTATCTGTGC CTGGT | TAGTGCTTCTCTTTGGT GCTGT |
|  | Gapdh | Qgapdh5/3 | ATGAATACGGCTACAG CAACAGG | CTCTTGCTCAGTGTCCT TGCTG |
|  | Gata2 | musGata2-qPCR-s1/as1 | AAAGTGTCCCAAGCTTC GAT | GCACTTGGTTGACTCA GCAC |
|  | Gata4 | Gata4b(+)/(-) | CCTAAACCTTACTGGCCGT AGC | ACAATGTTAACGGGTTGT GGAG |
|  | Kit | c-Kit(+)/(-) | CAGTTACCGCGCTCTGT TTG | GCCCCTTAAGTACCTG ACATCC |

-continued

|  | Target | Primer set name | sense primer | anti-sense primer |
|---|---|---|---|---|
|  | Myc | c-myc-1(+)/(-) | AAGGAGAACGGTTCCTTCTGAC | GCTGAAGCTTACAGTCCCAAAG |
|  | Nanog | Qnanog-5/3 | CTTTCACCTATTAAGGTGCTTGC | TGGCATCGGTTCATCATGGTAC |
|  | Pou5f1/Oct4 | Qoct4-5/3 | GATGCTGTGAGCCAAGGCAAG | GGCTCCTGATCAACAGCATCAC |
|  | Ppia | PPIA(+)/(-) | TTACCCATCAAACCATTCCTTCTG | AACCCAAAGAACTTCAGTGAGAGC |
|  | Prdm14 | prdm14-B(+)/(-) | ACAGCCAAGCAATTTGCACTAC | TTACCTGGCATTTTCATTGCTC |
|  | Rplp0/Arbp | PO(+)/(-) | CAAAGCTGAAGCAAAGGAAGAG | AATTAAGCAGGCTGACTTGGTTG |
|  | Sox2 | Qsox2-5/3 | CATGAGAGCAAGTACTGGCAAG | CCAACGATATCAACCTGCATGG |
| Human | POU5F1/OCT4 | hPOU5F1_F/R_qRT | CTGTCTCCGTCACCACTCTG | AAACCCTGGCACAAACTCCA |
|  | GAPDH | hsGAPDH-qPCR-s1/as1 | ACAAGAGGAAGAGAGACCCT | TCTACATGGCAACTGTGAGGAG |
|  | NANOG | hsNANOG-qPCR-s1 | AGAGGTCTCGTATTTGCTGCAT | AAACACTCGGTGAAATCAGGGT |
|  | SOX2 | hsSOX2-qPCR-s1/as1 | TGAATCAGTCTGCCGAGAATCC | TCTCAAACTGTGCATAATGGAGT |

Quantitative PCR (Q-PCR)

Q-PCR was performed using Power SYBR Green PCR Master mix [Life Technologies (4367659)] with a CFX384 real-time qPCR system [Bio-Rad] according to the manufacturer's instructions. The primer sequences are listed in Table 1.

Library Construction for the SC3-Seq for the SOLiD 5500XL System 5 ng of amplified and quality-checked cDNAs were added to the pre-amplification buffer [1×ExTaq buffer [Takara Bio (RR006)], 0.2 µM of each dNTP [Takara Bio (RR006)], 0.01 µg/µl of the N-V3 (dT)24 primer (HPLC-purified, attachment of amine at the 5' end), 0.01 µg/µl of the V1(dT)24 primer (HPLC-purified) and 0.025 U/µl of ExTaqHS [Takara Bio (RR006)]], and were amplified by four cycles of PCR. The byproduct such as primer dimers were removed by size selection through three rounds of purification using a 0.6× volume of AMPureXP beads for each round [Beckman Coulter (A63881)]. The purified cDNAs were diluted to 130 µl by double-distilled water (DDW) and fragmented by shearing with Covaris S2 or E210 [Covaris] and then endpolished in the End-polish buffer [1×NEBnext End Repair Reaction buffer [NEB (B6052S)], 0.01 U/µl of T4 DNA polymerase [NEB (M0203)] and 0.033 U/µl of T4 polynucleotide kinase [NEB (M0201)]] for 30 min at 20° C. After incubation, a 0.8×volume of the AMPureXP was added, the solution was mixed for more than 20 min and then the supernatant was transferred to a 1.2×volume of the AMPureXP and the cDNAs were purified. Next, to provide the purified cDNAs with an Int-adaptor sequence, the cDNAs were incubated in 30 µl of the Internal adaptor extension buffer [1×ExTaq Buffer, 0.23 mM of each dNTP, 0.67 µM of the IntV1 (dT)24 primer (HPLC-purified), 0.033 U/µl of ExTaqHS] using the following thermal cycler program: 95° C. for 3 min; 67° C. for 2 min; and 72° C. for 2 min. The reactions were terminated by chilling in an ice-block, and after the addition of 20 µl of the P1-adaptor ligation buffer [a mixture of 10 µl of 5×NEBNext Quick Ligation Reaction Buffer [NEB (B6058S)], 0.6 µl of 5 µM of the P1-T adaptor [Life Technologies (4464411)] and 1 µl of T4 ligase [NEB (M0202M)]], the solution was incubated for 15 min at 20° C. and for 20 min at 72° C. After two rounds of cDNA purification by adding a 1.2×volume of AMPure XP, the cDNAs were added into the Final amplification buffer [1×ExTaq buffer, 0.2 mM of each dNTP, 1 µM of the P1 primer, 1 µM of the BarTOXX IntV1 primer (HPLCpurified) (XX shows an integer of two digits, and specific primers are recited in Table 2), 0.025 U/µl of ExTaqHS] and amplified by PCR using the following thermal cycler program: 95° C. for 3 min; followed by nine cycles of 95° C. for 30 s, 67° C. for 1 min and 72° C. for 1 min; with a final extension of 72° C. for 3 min. Finally, the cDNA libraries were purified by using a 1.2×volume of AMPureXP and dissolved in 20 µl of TE buffer. The quality and quantity of the constructed libraries were evaluated by LabChip GX or Bioanalyzer 2100, a Qubit dsDNA HS assay kit [Life Technologies (Q32851)] and a SOLiD Library TaqMan Quantitation kit [Life Technologies (4449639)]. The amplification of the libraries on beads by emulsion PCR was performed using SOLiD™ EZ Bead™ System [Life Technologies (4449639)] at the E120 scale according to the manufacturer's instruction. The resulting bead libraries were loaded into flowchips and sequenced for 50 bp and 5 bp barcode plus Exact Call Chemistry (ECC) on an SOLiD 5500XL system [Life Technologies (4449639)].

Oligonitcleotids for SC3-seq library construction

| Oligonucleotids name | sequence |
| --- | --- |
| Table 2-1 | |
| V1(dT)24 | ATATGGATCCGGCGCGCCGTCGACTTTTTTTTTTTTTTTTTTTTTTTT |
| V3(dT)24 | ATATCTCGAGGGCGCGCCGGATCCTTTTTTTTTTTTTTTTTTTTTTTT |
| N-V3(dT)24 | (NH2)-ATATCTCGAGGGCGCGCCGGATCCTTTTTTTTTTTTTTTTTTTTTTTT |
| IntV1(dT)24 | CTGCTGTACGGCCAAGGCGTATATGGATCCGGCGCGCCGTCGACTTTTTTTTTTTTTTTTTTTTTTTT |
| P1 primer | CCACTACGCCTCCGCTTTCCTCTCTATG |
| BarT001-IntV1 | ctgccccgggttcctcattctctGTGTAAGAGGctgctgtacggccaaggcgtatatggatcc |
| BarT002-IntV1 | ctgccccgggttcctcattctctAGGGAGTGGTctgctgtacggccaaggcgtatatggatcc |
| BarT003-IntV1 | ctgccccgggttcctcattctctATAGGTTATActgctgtacggccaaggcgtatatggatcc |
| BarT004-IntV1 | ctgccccgggttcctcattctctGGATGCGGTCctgctgtacggccaaggcgtatatggatcc |
| BarT005-IntV1 | ctgccccgggttcctcattctctGTGGTGTAAGctgctgtacggccaaggcgtatatggatcc |
| BarT006-IntV1 | ctgccccgggttcctcattctctGCGAGGGACActgctgtacggccaaggcgtatatggatcc |
| BarT007-IntV1 | ctgccccgggttcctcattctctGGGTTATGCCctgctgtacggccaaggcgtatatggatcc |
| BarT008-IntV1 | ctgcccaggttcctcattctctGAGCGAGGATctgctgtacggccaaggcgtatatggatcc |
| BarT009-IntV1 | ctgccccgggttcctcattctctAGGTTGCGACctgctgtacggccaaggrgtatatggatcc |
| BarT010-IntV1 | ctgccccgggttcctcattctctGCGGTAAGCTctgctgtacggtcaaggcgtatatggatcc |
| BarT011-IntV1 | ctgccccgggttcctcattctctGTGCGACACGctgctgtacggccaaggcgtatatggatcc |
| BarT012-IntV1 | ctgccccgggttcctcattctctAAGAGGAAAActgctgtacggccaaggcgtatatggatcc |
| BarT013-IntV1 | ctgccccgggttcctcattctctGCGGTAAGGCctgctgtacggccaaggcgtatatggatcc |
| BarT014-IntV1 | ctgccccgggttcctcattctctGTGCGGCAGActgctgtacggccaaggcgtatatggatcc |
| BarT015-IntV1 | ctgccccgggttcctcattctctGAGTTGAATGctgctgtacggccaaggcgtatatggatcc |
| BarT016-IntV1 | ctgccccgggttcctcattctctGGGAGACGTTctgctgtacggcccaggcgtatatggatcc |
| BarT017-IntV1 | ctgccccgggttcctcattctctGGCTCACCGCctgctgtacggccaaggcgtatatggatcc |
| BarT018-IntV1 | ctgccccgggttcctcattctctAGGCGGATGActgctgtacggccaaggcgtatatggatcc |
| BarT019-IntV1 | ctgccccgggttcctcattctctATGGTAACTGctgctgtacggccaaggcgtatatggatcc |
| BarT020-IntV1 | ctgccccgggttcctcattctctGTCAAGCTTTctgctgtacggccaaggcgtatatggatcc |
| BarT021-IntV1 | ctgccccgggttcctcattctctGTGCGGTTCCctgctgtacggccaaggcgtatatggatcc |
| BarT022-IntV1 | ctgccccgggttcctcattctctGAGAAGATGActgctgtacggccaaggcgtatatggatcc |
| BarT023-IntV1 | ctgccccgggttcctcattctctGCGGTGCTTGctgctgtacggccaaggcgtatatggatcc |
| BarT024-IntV1 | ctgccccgggttcctcattctctGGGTCGGTATctgctgtacggccaaggcgtatatggatcc |
| BarT025-IntV1 | ctgccccgggttcctcattctctAACATGATGActgctgtacggccaaggcgtatatggatcc |
| BarT026-IntV1 | ctgccccgggttcctcattctctCGGGAGCCCGctgctgtacggccaaggcgtatatggatcc |
| BarT027-IntV1 | ctgccccgggttcctcattctctCAGCAAACTTctgctgtacggccaaggcgtatatggatcc |
| BarT028-IntV1 | ctgccccgggttcctcattctctAGCTTACTACctgctgtacggccaaggcgtatatggatcc |
| BarT029-IntV1 | ctgccccgggttcctcattctctGAATCTAGGGctgctgtacggccaaggcgtatatggatcc |
| BarT030-IntV1 | ctgccccgggttcctcattctctGTAGCGAAGActgctgtacggccaaggcgtatatggatcc |
| BarT031-IntV1 | ctgccccgggttcctcattctctGCTGGTGCGTctgctgtacggccaaggcgtatatggatcc |
| BarT032-IntV1 | ctgccccgggttcctcattctctGGTTGGGTGCctgctgtacggccaaggcgtatatggatcc |

| Oligonitcleotids for SC3-seq library construction | |
|---|---|
| Oligonucleotids name | sequence |
| BatT033-IntV1 | ctgccccgggttcctcattctctCGTTGGATACctgctgtacggccaaggcgtatatggatcc |
| BarT034-IntV1 | ctgccccgggttcctcattctctTCGTTAAAGGctgctgtacggccaaggcgtatatggatcc |
| BarT035-IntV1 | ctgccccgggttcctcattctctAAGCGTAGGActgctgtacggccaaggcgtatatggatcc |
| BarT036-IntV1 | ctgccccgggttcctcattctctGTTCTCACATctgctgtacggccaaggcgtatatggatcc |
| BarT037-IntV1 | ctgccccgggttcctcattctctCTGTTATACCctgctgtacggccaaggcgtatatggatcc |
| BarT038-IntV1 | ctgccccgggttcctcattctctGTCGTCTTAGctgctgtacggccaaggcgtatatggatcc |
| BarT039-IntV1 | ctgccccgggttcctcattctctTATCGTGAGTctgctgtacggccaaggcgtatatggatcc |
| BarT040-IntV1 | ctgccccgggttcctcattctctAAAAGGGTTActgctgthcggccaaggcgtatatggatcc |
| BarT041-IntV1 | ctgccccgggttcctcattctctTGTGGGATTGctgctgtacggccaaggcgtatatggatcc |
| BarT042-IntV1 | ctgccccgggttcctcattctctGAATGTACTActgctgtacggccaaggcgtatatggatcc |
| BarT043-IntV1 | ctgccccgggttcctcattctctCGCTAGGGTTctgctgtacggccaaggcgtatatggatcc |

Table 2-2

| | |
|---|---|
| BarT044-IntV1 | ctgccccgggttcctcattctctAAGGATGATCctactgtacggccaaggcgtatatggatcc |
| BarT045-IntV1 | ctgccccgggttcctcattctctGTACTTGGCTctgctgtacggccaaggcgtatatggatcc |
| BarT046-IntV1 | ctgccccgggttcctcattctctGGTCGTCGAActgctgtacggccaaggcgtatatggatcc |
| BarT047-IntV1 | ctgccccgggttcctcattctctGAGGGATGGCctgctgtacggccaaggcgtatatggatcc |
| BarT048-IntV1 | ctgccccgggttcctcattctctGCCGTAAGTGctgctgtacggccaaggcgtatatggatcc |
| BarT049-IntV1 | ctgccccgggttcctcattctctATGTCATAAGctgctgtacggccaaggcgtatatggatcc |
| BarT050-IntV1 | ctgccccgggttcctcattctctGAAGGCTTGCctgctgtacggccaaggcgtatatggatcc |
| BarT051-IntV1 | ctgccccgggttcctcattctctAAGCAGGAGTctgctgtacggccaaggcgtatatggatcc |
| BarT052-IntV1 | ctgccccgggttcctcattctctGTAATTGTAActgctgtacggccaaggcgtatatggatcc |
| BarT053-IntV1 | ctgccccgggttcctcattctctGTCATCAAGTctgctgtacggccaaggcgtatatggatcc |
| BarT054-IntV1 | ctgccccgggttcctcattctctAAAAGGCGGActgctgtacggccaaggcgtatatggatcc |
| BarT055-IntV1 | ctgccccgggttcctcattctctAGCTTAAGCGctgctgtacggccaaggcgtatatggatcc |
| BarT056-IntV1 | ctgccccgggttcctcattctctGCATGTCACCctgctgtacggccaaggcgtatatggatcc |
| BarT057-IntV1 | ctgccccgggttcctcattctctCTAGTAAGAActgctgtacggccaaggcgtatatggatcc |
| BarT058-IntV1 | ctgccccgggttcctcattctctTAAAGTGGCGctgctgtacggccaaggcgtatatggatcc |
| BatT059-IntV1 | ctgccccgggttcctcattctctAAGTAATGTCctgctgtacggccaaggcgtatatggatcc |
| BarT060-IntV1 | ctgccccgggttcctcattctctGTGCCTCGGTctgctgtacggccaaggcgtatatggatcc |
| BarT061-IntV1 | ctgccccgggttcctcattctctAAGATTATCGctgctgtacggccaaggcgtatatggatcc |
| BarT062-IntV1 | ctgccccgggttcctcattctctAGGTGAGGGTctgctgtacggccaaggcgtatatggatcc |
| BarT063-IntV1 | ctgccccgggttcctcattctctGCGGGTTCGActgctgtacggccaaggcgtatatggatcc |
| BarT064-IntV1 | ctgccccgggttcctcattctctGTGCTACACCctgctgtacggccaaggcgtatatggatcc |
| BarT065-IntV1 | ttgccccgggttcctcattctctGGGATCAAGCctgctgtacggccaaggcgtatatggatcc |
| BarT066-IntV1 | ctgccccgggttcctcattctctGATGTAATGTctgctgtacggccaaggcgtatatggatcc |
| BarT067-IntV1 | ctgccccgggttcctcattctctGTCCTTAGGGctgctgtacggccaaggcgtatatggatcc |
| BarT068-IntV1 | ctgccccgggttcctcattctctGCATTGACGActgctgtacggccaaggcgtatatggatcc |

-continued

| Oligonucleotids for SC3-seq library construction | |
|---|---|
| Oligonucleotids name | sequence |
| BarT069-IntV1 | ctgccccgggttcctcattctctGATATGCTTTctgctgtacggccaaggcgtatatggatcc |
| BarT070-IntV1 | ctgccccgggttcctcattctctGCCCTACAGActgctgtacggccaaggcgtatatggatcc |
| BarT071-IntV1 | ctgccccgggttcctcattctctACAGGGAACGctgctgtacggccaaggcgtatatggatcc |
| BarT072-IntV1 | ctgccccgggttcctcattctctAAGTGAATACctgctgtacggccaaggcgtatatggatcc |
| BarT073-IntV1 | ctgccccgggttcctcattctctGCAATGACGTctgctgtacggccaaggcgtatatggatcc |
| BarT074-IntV1 | ctgccccgggttcctcattctctAGGACGCTGActgctgtacggccaaggcgtatatggatcc |
| BarT075-IntV1 | ctgccccgggttcctcattctctGTATCTGGGCctgctgtacggccaaggcgtatatggatcc |
| BarT076-IntV1 | ctgccccgggttcctcattctctAAGTTTTAGGctgctgtacggccaaggcgtatatggatcc |
| BarT077-IntV1 | ctgccccgggttcctcattctctATCTGGTCTTctgctgtacggccaaggcgtatatggatcc |
| BarT078-IntV1 | ctgccccgggttcctcattctctGGCAATCATCctgctgtacggccaaggcgtatatggatcc |
| BarT079-IntV1 | ctgccccgggttcctcattctctAGTAGAATTActgctgtacggccaaggcgtatatggatcc |
| BarT080-IntV1 | ctgccccgggttcctcattctctGTTTACGGTGctgctgtacggccaaggcgtatatggatcc |
| BarT081-IntV1 | ctgccccgggttcctcattctctGAACGTCATTctgctgtacggccaaggcgtatatggatcc |
| BarT082-IntV1 | ctgccccgggttcctcattctctGTGAAGGGAGctgctgtacggccaaggcgtatatggatcc |
| BarT083-IntV1 | ctgccccgggttcctcattctctGGATGGCGTActgctgtacggccaaggcgtatatggatcc |
| BarT084-IntV1 | ctgccccgggttcctcattctctGCGGATGAACctgctgtacggccaaggcgtatatggatcc |
| BarT085-IntV1 | ctgccccgggttcctcattctctGGAAAGCGTTctgctgtacggccaaggcgtatatggatcc |
| BarT086-IntV1 | ctgccccgggttcctcattctctAGTACCAGGActgctgtacggccaaggcgtatatggatcc |
| BarT087-IntV1 | ctgccccgggttcctcattctctATAGCAAAGCctgctgtacggccaaggcgtatatggatcc |
| BarT088-IntV1 | ctgccctgggttcctcattctctGTTGATCATGctgctgtacggccaaggcgtatatggatcc |
| BarT089-IntV1 | ctgccccgggttcctcattctctAGGCTGTCTActgctgtacggccaaggcgtatatggatcc |
| BarT090-IntV1 | ctgccccgggttcctcattctctGTGACCTACTctgctgtacggccaaggcgtatatggatcc |
| BarT091-IntV1 | ctgccccgggttcctcattctctGCGTATTGGGctgctgtacggccaaggcgtatatggatcc |
| BarT092-IntV1 | ctgccccgggttcctcattctctAAGGGATTACctgctgtacggccaaggcgtatatggatcc |
| BarT093-IntV1 | ctgccccgggttcctcattctctGTTACGATGCctgctgtacggccaaggcgtatatggatcc |
| BarT094-IntV1 | ctgtccegggttcctcattctctATGGGTGTTTctgctgtacggccaaggcgtatatggatcc |
| BarT095-IntV1 | ctgccccgggttcctcattctctGAGTCCGGCActgctgtacggccaaggcgtatatggatcc |
| BarT096-IntV1 | ctgccccgggttcctcattctctAATCGAAGAGctgctgtacggccaaggcgtatatggatcc |

Library Construction for the SC3-Seq for Illumine Miseq System 2 ng of amplified and quality-checked cDNAs were added to the pre-amplification buffer [1×KOD FX NEO buffer, 0.4 μM of each dNTP [Takara Bio (RR006)], 0.3 μM of the N-P1 primer (HPLC-purified, attachment of amine at the 5' end), 0.3 μM of the P2 primer (HPLC-purified) and 0.02 U/μl of KOD FX Neo], and were amplified by four cycles of PCR. The PCR product was purified using a 0.6×volume of AMPureXP beads ((Beckman Coulter (A63881))]. The purified cDNAs were diluted to 130 μl by double-distilled water (DDW) and fragmented by shearing with Covaris S2 or E210 [Covaris] and then endpolished in the End-polish buffer [1×NEBnext End Repair Reaction buffer [NEB (B6052S)], 0.01 U/μl of T4 DNA polymerase [NEB (M0203)] and 0.033 U/μl of T4 polynucleotide kinase [NEB (M0201)]] for 30 min at 20° C. After incubation, a 0.7× volume of the AMPureXP was added, the solution was mixed for more than 20 min and then the supernatant was transferred to a 0.9×volume of the AMPureXP and the cDNAs were purified. Next, to provide the purified cDNAs with an Rd2SP-adaptor sequence, the cDNAs were incubated in 30 μl of the Internal adaptor extension buffer [1×ExTaq Buffer, 0.23 mM of each dNTP, 0.67 μM of the Rd2SP-P2 primer (HPLC-purified), 0.033 U/μl of ExTaqHS] using the following thermal cycler program: 95° C. for 3 min; 60° C. for 2 min; and 72° C. for 2 min. The reactions were terminated by chilling in an ice-block, and after the addition of 20 µl of the Rd1SP adaptor ligation buffer [a mixture of 10 µl of 5×NEBNext Quick Ligation Reaction Buffer [NEB (B6058S)], 0.6 µl of 10 µM of the Rd1SP adaptor and 1 µl of T4 ligase [NEB (M0202M)]], the solution was incubated for 15 min at 20° C. and for 20 min at 72° C. After two rounds of cDNA purification by adding a 0.8×volume of AMPure XP, the cDNAs were added into the Final amplification buffer [1×KOD Fx Neo buffer, 0.4 mM of each dNTP, 0.3125 µM of the SSXX primer (XX shows an integer of two digits, and specific primers are recited in Table 3), 0.3125 µM of the N7XX primer (HPLC-purified) (XX shows an integer of two digits, and specific primers are recited in Table 3), 0.02 U/µl of KOD FX NEO] and amplified by PCR using the following thermal cycler program: incubation at 95° C. for 3 min; followed by nine cycles of 95° C. for 10 sec, 60° C. for 1 min and 68° C. for 1 min; with a final extension of 68° C. for 3 min. Finally, the cDNA libraries were purified by using a 0.9×volume of AMPureXP and dissolved in 20 µl of TE buffer. The quality and quantity of the constructed libraries were evaluated by LabChip GX or Bioanalyzer 2100, a Qubit dsDNA HS assay kit [Life Technologies (Q32851)] and a KAPA Library Quantification Kits [KAPA (KK4828)]. The resulting library DNAs were analyzed using Miseq Reagent kit v3, 150 cycles (Illumina (MS-102-3001)).

TABLE 3

Oligonucleotids for SC3-seq library construction

| Oligonucleotids name | sequence |
| --- | --- |
| P1(dT)24 | CCACTACGCCTCCGCTTTCCTCTCTATGGHTTTTTTTTTTTTTTTTTTTTTT |
| P2(dT)24 | CTGCCCCGGGTTCCTCATTCTTTTTTTTTTTTTTTTTTTTTTTT |
| P1(28) | CCACTACGCCTCCGCTTTCCTCTCTATG |
| P2(21) | CTGCCCCGGGTTCCTCATTCT |
| tRd2SP-P2 | GTGACTGGAGTTCAGACGTGTGCTCTTCCGATCCTGCCCCGGGTTCCTCATTCT |
| tRd1SPTs | TCTTTCCCTACACGACGCTCTTCCGATcT |
| tRd1SPTas | GATCGGAAGAGCGTCGTGTAGGGAAAGA |
| tRd2SPV1(dT)20 | GTGACTGGAGTTCAGACGTGTGCTCTTCCGATCATATGGATCCGGCGCGCCGTCGACTTTTTTTTTTTTTTTTTTTT |
| S502 | AATGATACGGCGACCACCGAGATCTACACCTCTCTATACACTCTTTCCCTACACGACGCTCT |
| S503 | AATGATACGGCGACCACCGAGATCTACACTATCCTCTACACTCTTTCCCTACACGACGCTCT |
| S505 | AATGATACGGCGACCACCGAGATCTACACGTAAGGAGACACTCTTTCCCTACACGACGCTCT |
| S506 | AATGATACGGCGACCACCGAGATCTACACACTGCATAACACTCTTTCCCTACACGACGCTCT |
| S507 | AATGATACGGCGACCACCGAGATCTACACAAGGAGTAACACTCTTTCCCTACACGACGCTCT |
| S508 | AATGATACGGCGACCACCGAGATCTACACCTAAGCCTACACTCTTTCCCTACACGACGCTCT |
| S510 | AATGATACGGCGACCACCGAGATCTACACCGTCTAATACACTCTTTCCCTACACGACGCTCT |
| S511 | AATGATACGGCGACCACCGAGATCTACACTCTCTCCGACACTCTTTCCCTACACGACGCTCT |
| S513 | AATGATACGGCGACCACCGAGATCTACACTCGACTAGACACTCTTTCCCTACACGACGCTCT |
| S515 | AATGATACGGCGACCACCGAGATCTACACTTCTAGCTACACTCTTTCCCTACACGACGCTCT |
| S516 | AATGATACGGCGACCACCGAGATCTACACCCTAGAGTACACTCTTTCCCTACACGACGCTCT |
| S517 | AATGATACGGCGACCACCGAGATCTACACGCGTAAGAACACTCTTTCCCTACACGACGCTCT |
| S518 | AATGATACGGCGACCACCGAGATCTACACCTATTAAGACACTCTTTCCCTACACGACGCTCT |
| S520 | AATGATACGGCGACCACCGAGATCTACACAAGGCTATACACTCTTTCCCTACACGACGCTCT |
| S521 | AATGATACGGCGACCACCGAGATCTACACGAGCCTTAACACTCTTTCCCTACACGACGCTCT |
| S522 | AATGATACGGCGACCACCGAGATCTACACTTATGCGAACACTCTTTCCCTACACGACGCTCT |
| N701 | CAAGCAGAAGACGGCATACGAGATTCGCCTTAGTGACTGGAGTTCAGACGTGT |
| N702 | CAAGCAGAAGACGGCATACGAGATCTAGTACGGTGACTGGAGTTCAGACGTGT |
| N703 | CAAGCAGAAGACGGCATACGAGATTTCTGCCTGTGACTGGAGTTCAGACGTGT |
| N704 | CAAGCAGAAGACGGCATACGAGATGCTCAGGAGTGACTGGAGTTCAGACGTGT |
| N705 | CAAGCAGAAGACGGCATACGAGATAGGAGTCCGTGACTGGAGTTCAGACGTGT |

TABLE 3-continued

Oligonucleotids for SC3-seq library construction

| Oligonucleotids name | sequence |
|---|---|
| N706 | CAAGCAGAAGACGGCATACGAGATCATGCCTAGTGACTGGAGTTCAGACGTGT |
| N707 | CAAGCAGAAGACGGCATACGAGATGTAGAGAGGTGACTGGAGTTCAGACGTGT |
| N710 | CAAGCAGAAGACGGCATACGAGATCAGCCTCGGTGACTGGAGTTCAGACGTGT |
| N711 | CAAGCAGAAGACGGCATACGAGATTGCCTCTTGTGACTGGAGTTCAGACGTGT |
| N712 | CAAGCAGAAGACGGCATACGAGATTCCTCTACGTGACTGGAGTTCAGACGTGT |
| N714 | CAAGCAGAAGACGGCATACGAGATTCATGAGCGTGACTGGAGTTCAGACGTGT |
| N715 | CAAGCAGAAGACGGCATACGAGATCCTGAGATGTGACTGGAGTTCAGACGTGT |
| N716 | CAAGCAGAAGACGGCATACGAGATTAGCGAGTGTGACTGGAGTTCAGACGTGT |
| N718 | CAAGCAGAAGACGGCATACGAGATGTAGCTCCGTGACTGGAGTTCAGACGTGT |
| N719 | CAAGCAGAAGACGGCATACGAGATTACTACGCGTGACTGGAGTTCAGACGTGT |
| N720 | CAAGCAGAAGACGGCATACGAGATAGGCTCCGGTGACTGGAGTTCAGACGTGT |
| N721 | CAAGCAGAAGACGGCATACGAGATGCAGCGTAGTGACTGGAGTTCAGACGTGT |
| N722 | CAAGCAGAAGACGGCATACGAGATCTGCGCATGTGACTGGAGTTCAGACGTGT |
| N723 | CAAGCAGAAGACGGCATACGAGATGAGCGCTAGTGACTGGAGTTCAGACGTGT |
| N724 | CAAGCAGAAGACGGCATACGAGATCGCTCAGTGTGACTGGAGTTCAGACGTGT |
| N726 | CAAGCAGAAGACGGCATACGAGATGTCTTAGGGTGACTGGAGTTCAGACGTGT |
| N727 | CAAGCAGAAGACGGCATACGAGATACTGATCGGTGACTGGAGTTCAGACGTGT |
| N728 | CAAGCAGAAGACGGCATACGAGATTAGCTGCAGTGACTGGAGTTCAGACGTGT |
| N729 | CAAGCAGAAGACGGCATACGAGATGACGTCGAGTGACTGGAGTTCAGACGTGT |

Mapping to the Reference Genome

The adaptor or the poly-A sequences were trimmed by cutadapt-1.3, and all the reads were surveyed. The trimmed reads with less than 30 bp were discarded. The adaptor and the poly-A sequences were observed in about 1-20% and 5% of the total reads, respectively. Untrimmed and trimmed reads of 30 bp or longer were mapped onto the mouse genome mm10 and the ERCC spike-inRNA with tophat-1.4.1/bowtie1.0.1 with the '-no-coverage-search' option. Mapped reads on the genome and the ERCC were separated, and the reads on the genome were converted into the expression levels by cufflinks-2.2.0 using the '-compatible-hits-norm', '-no-length-correction' and '-library-type frsecondstrand' options and mm10 reference gene annotations with extended TTSs. The cufflinks option '-max-mle-iterations' were set to 50,000, because default iterations (5,000) resulted in 'FAILED' when the expression levels of some genes were estimated. For the reference gene annotations using cufflinks, the TTSs of the reference genes were extended to not less than 10 kb downstream to correctly estimate the expression levels of genes whose transcripts are longer than the reference toward the 3' direction. To estimate the transcript copy number per cell, the ERCC spike-in RNA reads were normalized to reads per million-mapped reads (RPM) by total reads mapped on the genome used for gene expression analysis. The mapped reads were visualized using igv-2.3.34. The conversion of the mapped reads into the expression levels by HTSeq-0.6.0 was consistent with the results by cufflinks-2.2.0 using the options described above.

Analysis of Data Obtained by SC3-Seq and Conventional Method

Figure 4:
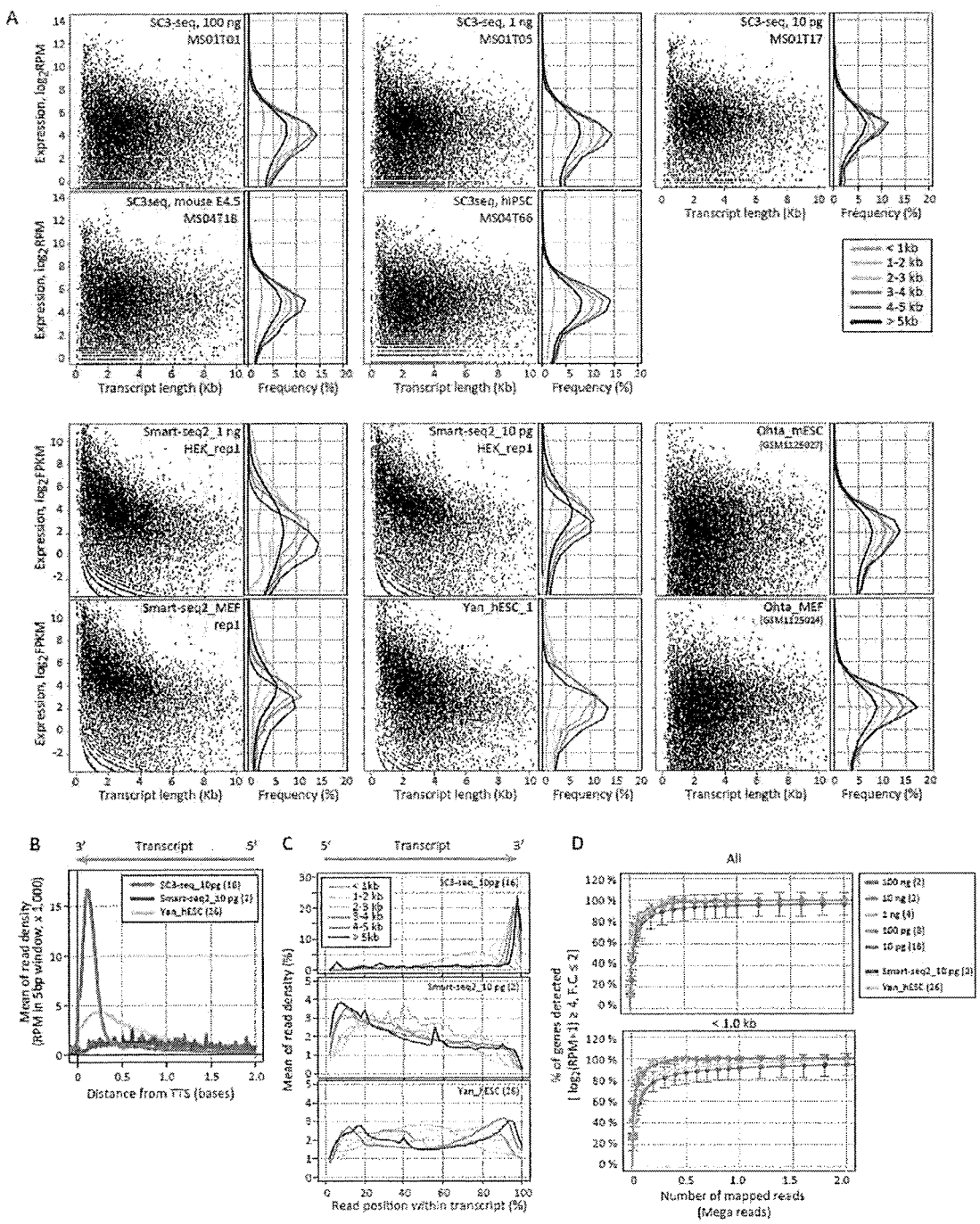
FIG. 4A is a graph showing the plot of the expression level and the transcript length, which are detected in dilution samples from SC3-seq (100 ng (replicated once, MS01T01), 10 ng (replicated once, MS01T05) and 10 pg (replicated once, MS01T17) of ESC total RNAs; dilution samples from single mESC (MS04T18) and single human ESC (MS04T66)), Smart-seq2 (1 ng (Smart-seq2_1 ng, HEK_rep1) and 10 pg (Smart-seq2_10 pg, HEK_rep1) of HEK293 total RNAs; and single mESC and single mouse embryonic fibroblast (Smart-seq2_MEF, replicated once)), single cell RNA-seq by Yan et al. (single human ESC (Yan_hESC_1) and full length RNA-seq (Ohta_mESC and Ohta_MEF]. The expression levels by SC3-seq are shown as $\log_2$ RPM, whereas those by the other methods are shown as $\log_2$ FPKM. The histogram on the right of each scatter plot indicates distribution of gene expression levels of transcripts with different lengths.
FIG. 4B is a graph showing distributions of the mapped reads around the 3'-ends of the transcripts by the three single-cell RNA-seq method.
FIG. 4C is a graph showing distributions of the mapped reads by the length of the transcripts by the three single-cell RNA-seq method.
FIG. 4D is a graph showing analysis of detection limit by the three single-cell RNA-seq method of all (top) and short transcripts (less than 1 kbp, 913 and 832 genes for mouse and human, respectively) (bottom) [gene-expression levels of not less than the 6555th from the top and not less than the 6217th for mice and humans, respectively (¼ of all the annotated transcripts for mice and humans), $\sim\log_2$ RPM≥3.69±0.05 (SC3-seq), $\sim\log_2$ FPKM≥2.21±1.28 (Yan et al.) and $\sim\log_2$ FPKM≥2.92±0.27 (Picelli et al.), 2-fold compared to gene expression levels by the full length reads).
Figure 10:
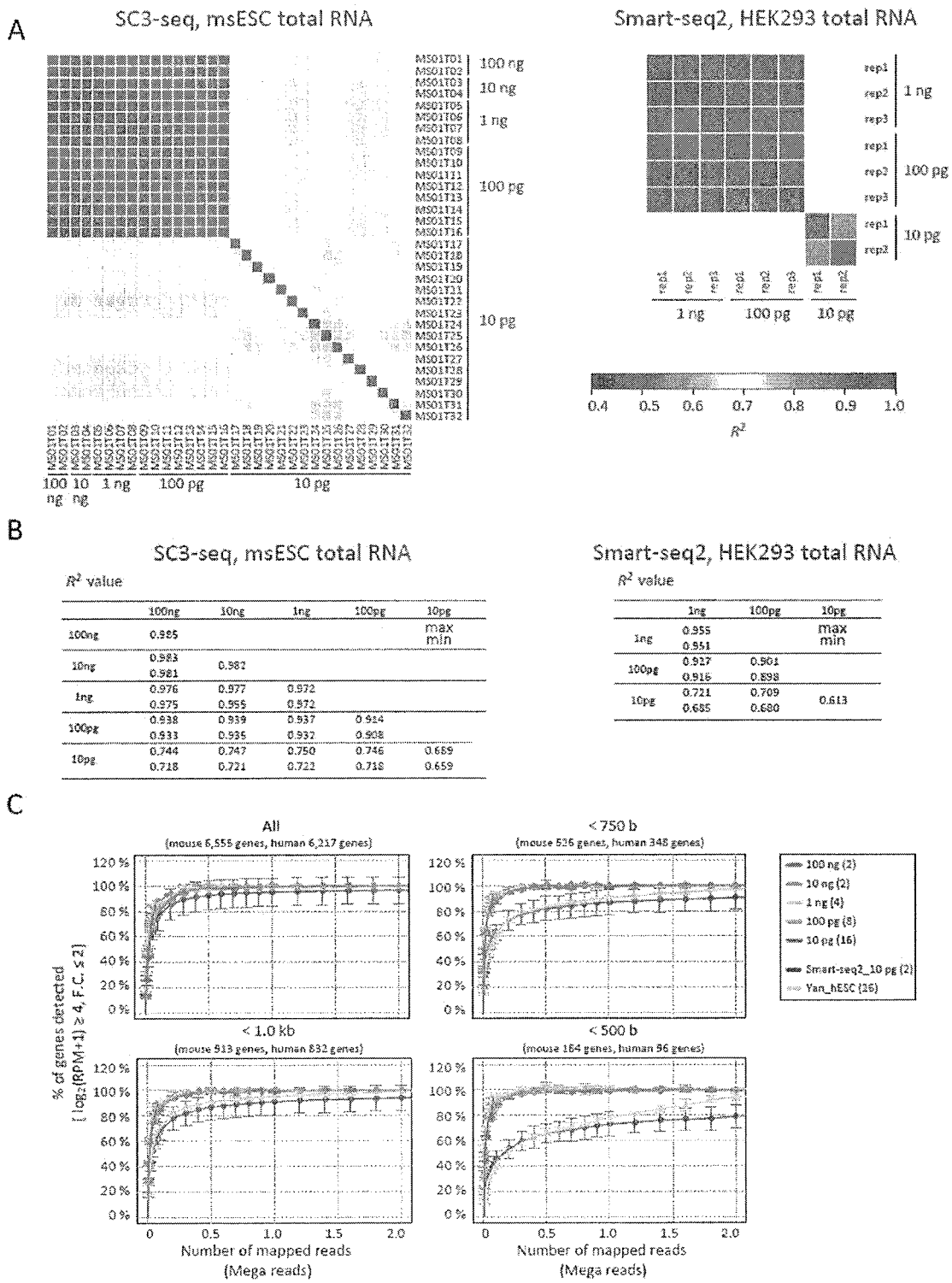
FIG. 10A shows a heat-map of the correlation coefficients among amplified dilution samples and measured dilution samples by SC3-seq (left) and Smart-seq2 (right). Expression values less than 0.1 RPM and 0.1 FPKM by SC3-seq and Smart-seq2, respectively, were set as 0.1.
FIG. 10B shows the minimum (min) and maximum (max) values of correlation coefficients in pair-wise comparison groups shown in FIG. 10A (left: SC3-seq; right: Smart-seq2).
FIG. 10C shows the results of detection limit analysis by three RNA-seqs of all transcription product (upper panel, left), less than 1 Kbp transcription product (lower panel, left), less than 750 bp transcription product (upper panel, right) and less than 500 bp transcription product (lower panel, right) (gene expression levels of not less than the top 6555th and not less than the 6217th for mice and humans, respectively (¼ of all the annotated transcripts for mice and humans), ~$\log_2$ RPM≥3.69±0.05 (SC3-seq), ~$\log_2$ FPKM≥2.21±1.28 (Yan et al.), and ~$\log_2$ FPKM≥2.92±0.27 (Picelli et al.), ≤2-fold compared to gene expression level by full length reads).

Analysis was performed using R software version 3.0.2 and Excel (Microsoft). The expression data by the SC3-seq were analyzed using $\log_2$ (RPM+1) as the expression value, except in FIG. 4, FIGS. 10A and 10B. In FIG. 4, the RPM/FPKM values less than 0.01 were set as 0.01 for the calculation of correlation coefficients. In FIGS. 10A and 10B, the RPM/FPKM values less than 0.1 were set as 0.1 for the calculation of correlation coefficients.

The estimation of the optimum definition of the 3' ends of the transcripts was performed by modifying the reference gene annotation gff3 file. All gene expression values were calculated when the definition of the 3' ends of the transcripts was extended in 1 kb increments up to 10 kb, then in 10 kb increments up to 100 kb. Genes whose expression levels were increased by 10, 20, 30, 40, 50, 80, 100, 200 and 300% were counted.

The estimation of the copy numbers per 10 pg total RNAs was performed by drawing a single linear regression line for all $\log_e$ (RPM+1) values of the ERCC spike-in RNAs (excluding the ERCC spike-in RNAs whose copy numbers are lower than 100 copy per 10 pg RNAs and the two outliers ERCC-00116 and ERCC-00004) in all the 32 amplified samples as a function of their copy numbers. The $\log_2$ (RPM+1) values for 1000 copies, 100 copies, 10 copies and one copy per 10 pg total RNA were 11.78, 8.10, 4.43 and 0.76, respectively.

The coverage is defined by the number of genes detected in samples amplified from 10 pg of total RNAs [$\log_2$ (RPM+1)≥1] as a percentage of that in samples amplified from 100 ng of total RNAs [$\log_2$ (RPM+1)≥1] for different expression-level ranges. Accuracy is defined based on the number of genes detected in samples amplified from 100 ng of total RNAs [$\log_{2\ (RPM+}1)$≥1] as a percentage of that in samples amplified from 10 pg of total RNAs [$\log_2$ (RPM+1)≥1]. The expressed genes were defined as those that were detected [$\log_2$ (RPM+1)≥1] in samples prepared by SC3-seq from 100 ng of RNAs. Multiple sample analyses (eight samples) for the coverage and the accuracy were performed by calculating the coverage and accuracy under definitions of detection where 1 to 8 of the eight amplified samples exhibited reads.

For analysis of the saturation of the detection of gene expression, conversion of the mapped reads to gene expression levels by cufflinks was repeated with the number of mapped reads reduced to as low as 10,000. The numbers of genes detected at significant expression levels [$\log_2$ (RPM+1)>4] were counted under different numbers of total mapped reads. When comparing the data by the SC3-seq with the published data by other methodologies, $\log_2$ RPM was used as an expression value for the SC3-seq and the top 6555th and 6217th genes were included for mice and humans, respectively, for the analysis.

Data Analysis of the SC3-Seq Results for the Single Cells in the E4.5 Blastocysts, Human iPS Cells and Macaca Fascicularisearis Embryo Analysis was performed using R software version 3.1.1 with the Gplots and the qvalue packages, and EXCEL. All the analyses of expression data were performed using $\log_2$ (RPM+1) values. Genes whose $\log_2$ (RPM+1) value was less than 4 (less than about 20 copies/cell) in samples were excluded from the analysis. Unsupervised hierarchical clustering (UHC) was performed using the hclust function with Euclidean distances and Ward distance functions (ward.D2). The principal component analysis (PCA) was performed using the prcomp function without scaling.

To identify differentially expressed genes (DEGs) among multi-groups, the oneway analysis of variance (ANOVA) and the qvalue function were used for the calculation of the P value and false discovery ratio (FDR), respectively. The DEGs were defined as those exhibited a more than 4-fold change between the samples (FDR<0.01), and the mean of the expression level of the group was ≥$\log_2$ (RPM+1)=4. The gene ontology (GO) analysis was performed using the DAVID web tool.

Immunofluorescence Analysis of Mouse E4.5 Embryos

For whole-mount immunofluorescence (IF) analysis, isolated embryos were fixed in 4% paraformaldehyde in PBS for 20 min at room temperature, washed in 2% BSA/PBS and incubated in the permeabilization solution (0.5% Triton X/1.0% BSA/PBS) for 20 min at room temperature. After washing twice in 2% BSA/PBS, embryos were incubated with primary antibodies in 2% BSA/PBS overnight at 4%, washed three times with 2% BSA/PBS, incubated with secondary antibodies and 4,6-diamidino-2-phenylindole (DAPI) in 2% BSA/PBS for 1 hr at room temperature, washed three times with 2% BSA/PBS and mounted in VECTASHIELD Mounting Medium [Vector Laboratories, (H-1000)]. The primary antibodies used were as follows: anti-mouse NANOG [rat monoclonal; eBioscience, (eBio14-5761)], anti-mouse POU5F1 [mouse monoclonal; Santa Cruz, (sc-5279)], anti-mouse GATA4 [goat polyclonal; Santa Cruz, (sc-1237)], anti-mouse CDX2 [rabbit monoclonal, clone EPR2764Y; Abcam, (ab76541)]. The secondary antibodies used were as follows: Alexa Fluor 488 anti-rat IgG [Life Technologies (A21208)], Alexa Fluor 555 anti-rabbit [Life Technologies (A31572)], Alexa Fluor 568 anti-mouse IgG [Life Technologies (A10037)] and Alexa Fluor 647 anti-goat IgG [Life Technologies (A21447)] (all donkey polyclonal). Image data were obtained and processed by a confocal microscope [Olympus, (FV1000)].

Accession Numbers

As the accession numbers, the following data generally used in the pertinent field were used; SC3-seq data (GSE63266, GSE74767), RNA-seq data for mESCs and mouse embryonic fibroblasts (MEFs) (GSE45916) (Ohta, S., et al., Cell reports, 5, 357-366, 2013), SMART-seq2 data for MEF (GSE49321) (Picelli, S., et al., Nat Methods, 10, 1096-1098, 2013) and single-cell RNA-seq data for hESCs. (GSE36552) (Yan, L., et al., Nat Struct Mol Biol, 20, 1131-1139, 2013).

EXAMPLE 2

Design and Construction of SC3-Seq

For the amplification of single cell cDNA, a method including condensing high density oligonucleotide microarray-like 3'-end side was used (Kurimoto, K., et al., Nucleic Acids Res, 34, e42, 2006 and Kurimoto, K., et al., Nature protocols, 2, 739-752, 2007). This method is useful for the developmental analysis of cells with diversity, for example, analysis of non-uniform cell type such as mouse blastocyst and the like, elucidation of transcriptome in the development of primordial germ cell (PGC), elucidation of nerve cell species in the development of cerebral cortex and the like. This method has been shown to be useful not only for the transcriptome analysis in a single cell but also when the target includes many cells. The method has been modified so that longer cDNAs including full-length cDNAs are synthesized and analyzed by RNA-seq. However, considering the inefficiency of full-length cDNA synthesis and susceptibility to amplification bias of longer cDNAs, amplification and sequencing of the 3' ends of cDNAs are considered to provide more precise assessment of gene-expression levels (FIG. 1A). Furthermore, sequencing of only the 3' ends theoretically requires a much smaller sequence depth for saturation (FIG. 1B), making the analysis more cost-effective.

A method of amplifying and sequencing the 3'-terminal of cDNA synthesized from a single cell is called SC3-seq and the method is shown in FIG. 1C. For cDNA amplification, cDNA was amplified from a single cell level RNA by a conventional method (FIG. 1C). The first-strand cDNAs were synthesized by the V1 (dT)24 primer, the excess V1 (dT)24 primer and the annealed mRNAs were digested by Exonuclease I and RNaseH, respectively, the poly (dA) tail was added at the 3' ends of the first-strand cDNAs, the second-strand cDNAs were synthesized by the V3 (dT)24 primer and the resultant cDNAs were amplified by the V1 (dT)24 and V3(dT)24 primer pair by a number of PCR cycles depending on the amount of the starting materials (20 cycles for single cells or 10 pg of total RNA). For the construction of the library for sequencing by the SOLiD sequencer, a procedure that enriches the very 3' ends of the cDNAs bearing the V1(dT)24 primer (FIG. 1C and FIG. 7A) was designed. The amplified cDNAs were tagged by the NH2-V3(dT)24 primer with a few PCR cycles, the primer dimers were removed by three rounds of purification by AMPureXP and the tagged cDNAs were fragmented by sonication, endpolished and size-fractionated by sequential purification by AMPure XP. The resultant cDNAs of 200-

Figure 7:
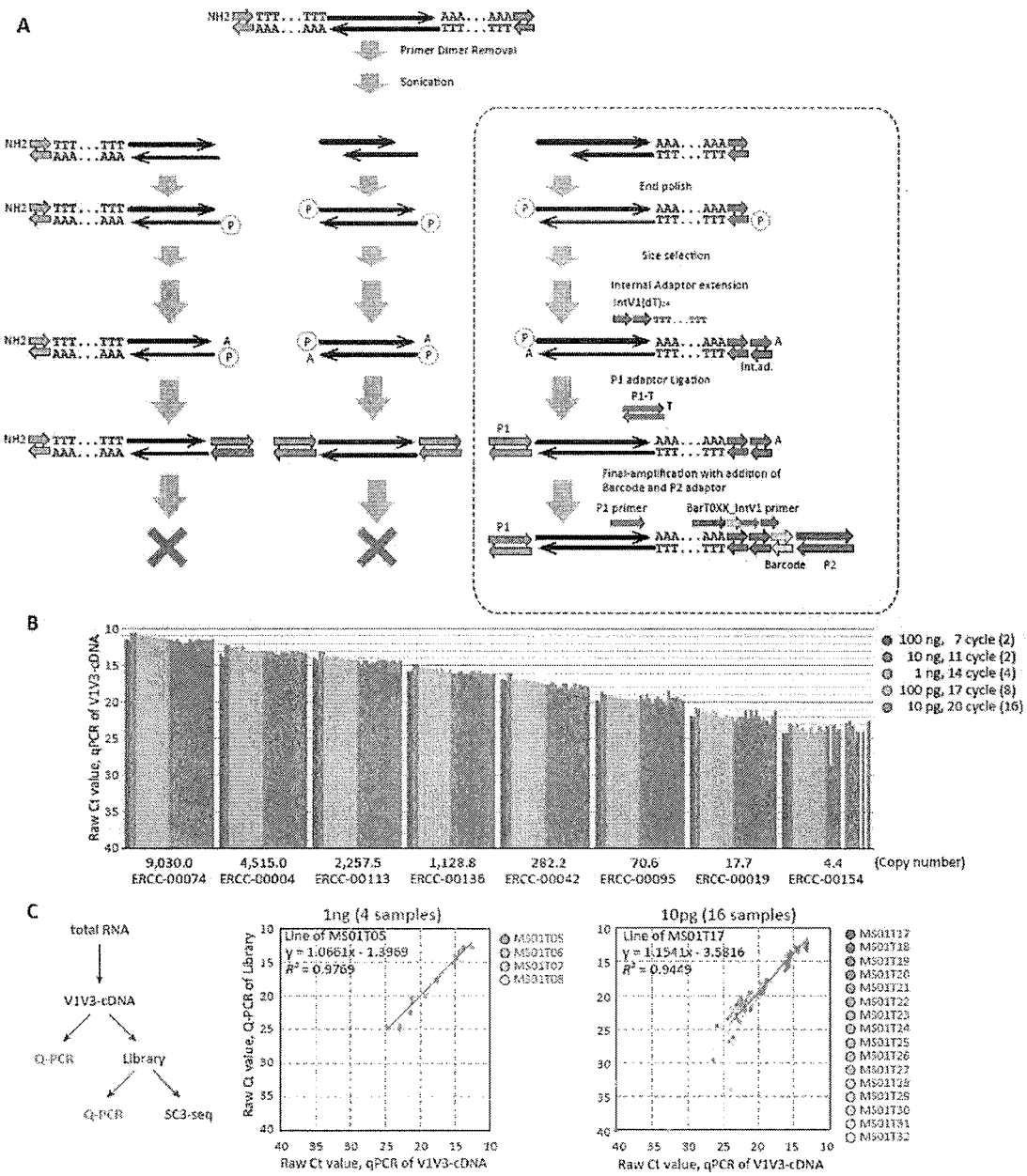
FIG. 7A shows the outline of the mechanism enabling library construction by SC3-seq on the 3' ends. After fragmentation, there occur three types of fragments: fragments bearing V3 tag on the 5' ends, fragments without a tag, and fragments bearing a V1-tag. All of these are polished and phosphorylated at the blunt ends. In an internal adaptor extension step, Int sequence is added only to fragments bearing the 3' ends added with a V1 tag. In a P1 adaptor ligation step, P1 adaptor is added to the fragments bearing the V3-tagged ends and also to inner fragments in the polished sites. However, since the 3' sides of the fragments having IntV1 tag are free of a phosphoric acid group, P1 adaptor is not added to them. Finally, only the fragments harboring both P1 and IntV1 tags are amplified, whereby library can be constructed selectively at the 3' ends.
FIG. 7B shows the results of Q-PCR of the amplification levels of the ERCC spike-in RNAs amplified from 100 ng, 10 ng, 1 ng, 100 pg, and 10 pg of ESC total RNAs.
FIG. 7C is a graph showing comparison of the expression levels of amplified cDNAs [1 ng (middle, 4 samples) and 10 pg (right, 16 samples) total RNAs] with the expression levels of SC3-seq library (CT value of Q-PCR) (MS01T05 and MS01T17 for 1 ng and 10 pg, respectively, of total RNAs). The left Figure shows a concept drawing of the comparison method.
Figure 8:
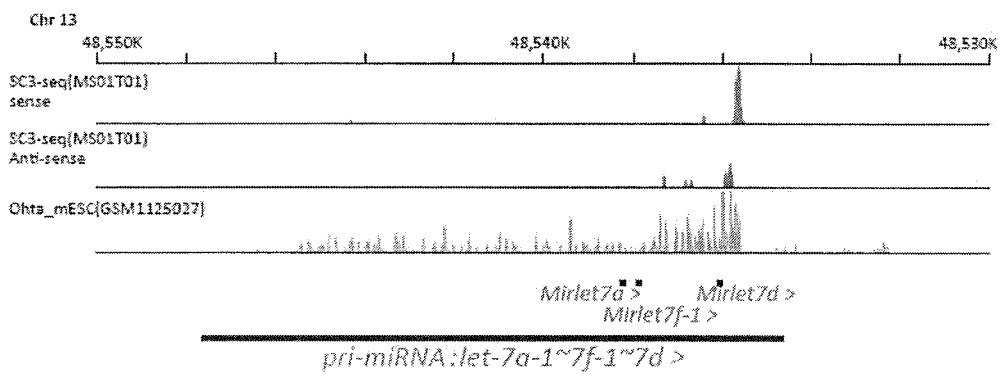
FIG. 8A shows detection of reads on Let7a-7d gene loci. The upper panel shows mapping of SC3-seq on the sense strand, the middle panel shows mapping of SC3-seq on the antisense strand, the lower panel shows mapping by Ohta et al.
FIG. 8B shows detection of reads on Mir290-295 gene locus. The noncoding D7Ertd143e is a Mir290-295 precursor. The upper panel shows mapping by SC3-seq on the sense strand, the middle panel shows mapping by SC3-seq on the antisense strand, and the lower panel shows mapping by Ohta et al.
FIG. 8C shows detection of reads on Mir684-1 gene locus. Single miRNA is encoded by intron of a gene encoding Dusp19. The upper panel shows mapping by SC3-seq on the sense strand, the middle panel shows mapping by SC3-seq on the antisense strand, and the lower panel shows mapping by Ohta et al.
FIG. 8D shows detection of reads on an unclassified non-coding RNA, Gm19693, which is annotated at the reverse strand of the 3' end of the H2afz. The upper panel shows mapping by SC3-seq on the sense strand, and the middle panel shows mapping by SC3-seq on the antisense strand, and the lower panel shows mapping by Ohta et al.
Figure 8:
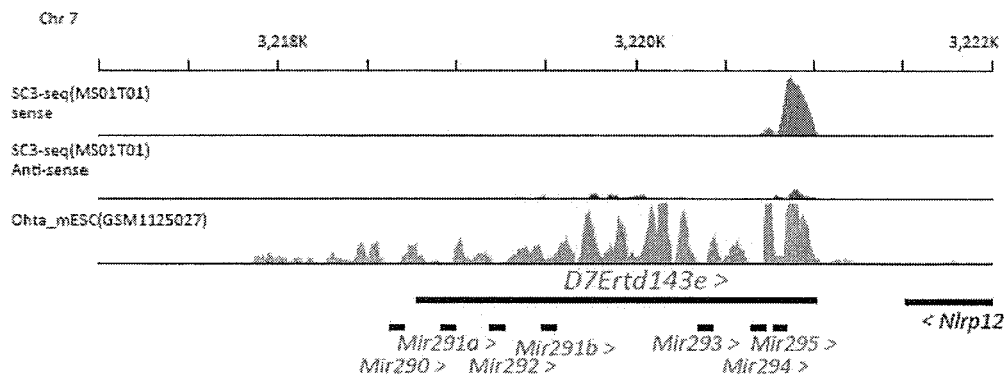
Figure 8:
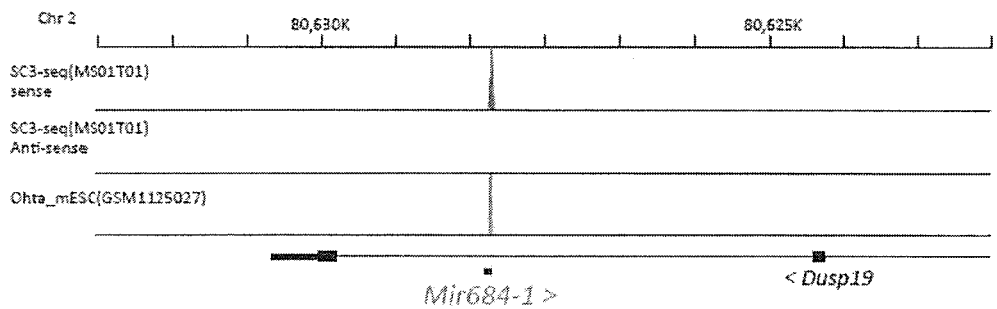
Figure 8:
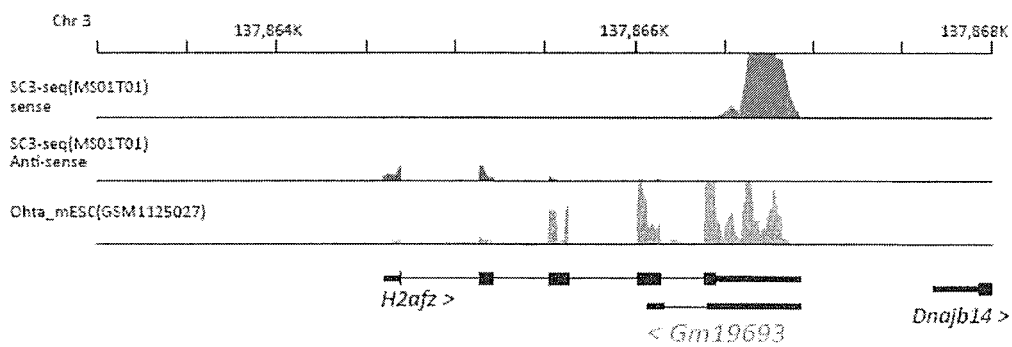
Figure 9:
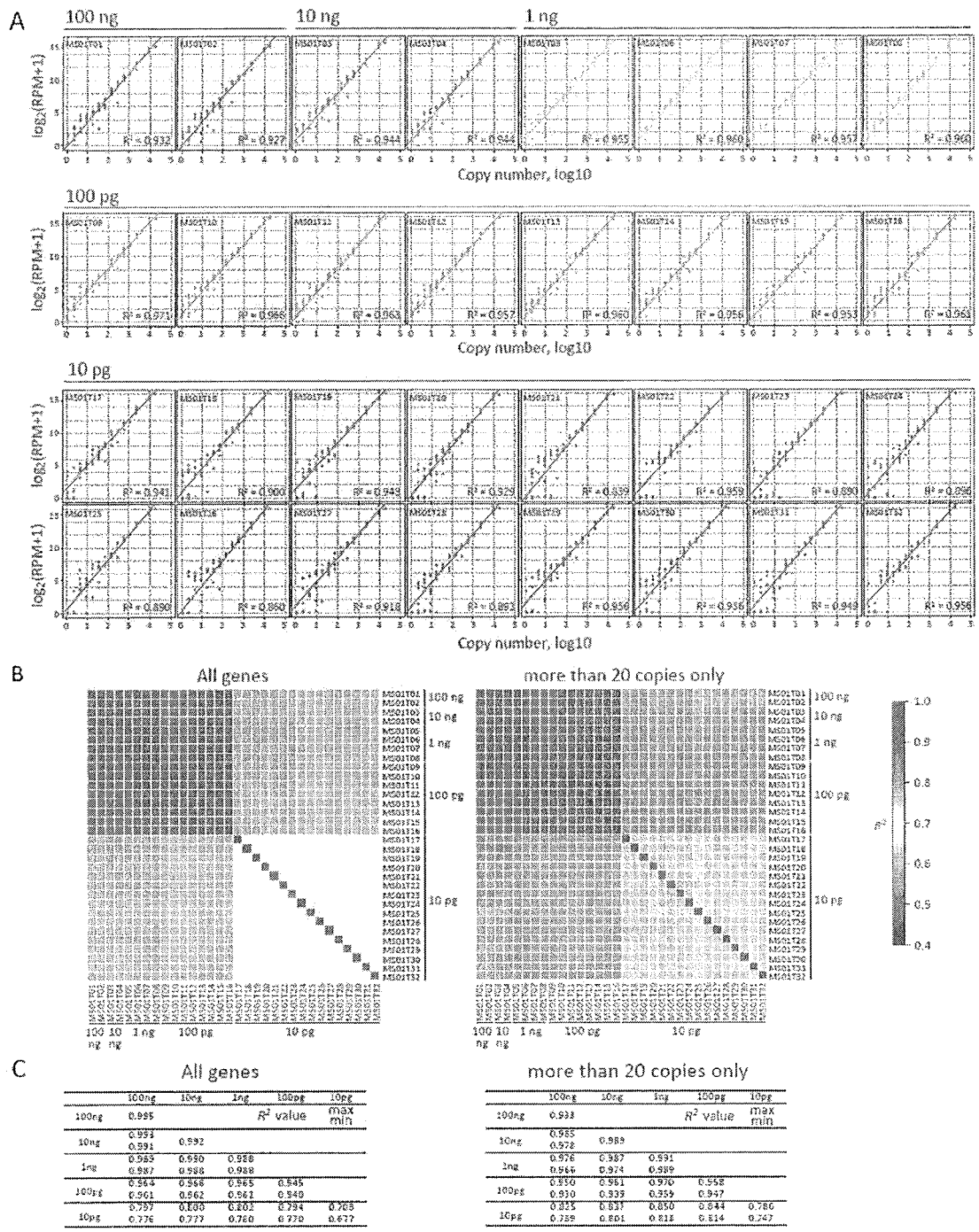
FIG. 9A shows the relationship between the quantities of ERCC RNAs of mESC total RNAs (100 ng:two replicates; 10 ng:two replicates; 1 ng:four replicates; 100 pg:eight replicates; 10 pg:sixteen replicates) after spiked in a dilution and the calculated levels of ERCC spike-in RNAs by SC3-seq ($\log_2$(RPM+1)). The SC3-seq data for ERCC spike-in RNAs with not less than 10 copies per 10 pg were utilized for the regression line.
FIG. 9B shows a heat-map of the correlation coefficients ($R^2$) among all measured samples and all amplified samples by SC3-seq from dilution products of ESC total RNAs (left: data of all expressed genes; right: data of genes expressing not less than 20 copies per 10 pg).
FIG. 9C shows the minimum (min) and maximum (max) values of correlation coefficients in pair-wise comparison groups shown in FIG. 9B (left: data of all expressed genes; right: data of genes expressing not less than 20 copies per 10 pg).

250 bp were denatured, annealed by the IntV1(dT)24 primer for the capture of the 3' ends with the extension of the internal adaptor extension sequence, ligated and sequence extended with the P1 adaptor and processed for final amplification by the P1 primer and the BarTOXX-IntV1 primer bearing 96 distinct barcodes. The final amplified products were sequenced from the P1-adaptor end, resulting in the mapping of the 3' ends of the mRNAs on the genomic loci. Since the SC3-seq provides sequence reads only at the 3' ends of mRNAs, the absolute read counts become proportional to the expression levels of mRNAs irrespective of their entire length, allowing simple and more accurate quantification of the gene-expression levels. Accurate quantification was performed by normalization based on the sequence reads per 1,000,000 mapped reads. To evaluate SC3-seq, two replicates of total RNAs [100 ng (corresponding to 10,000 cells), two replicates of 10 ng (corresponding to 1,000 cells), four replicates of 1 ng (corresponding to 100 cells), eight replicates of 100 pg (corresponding to 10 cells) and 16 replicates of 10 pg (corresponding to single cells) were isolated from mESCs, RNA was collected together with external spike-in RNA controls developed by External RNA Controls Consortium (ERCC), amplified (7, 11, 14, 17 and 20 initial PCR cycles for 100 ng, 10 ng, 1 ng, 100 pg and 10 pg total RNAs, respectively) and sequenced by SC3-seq. It was confirmed by quantitative PCR that the ERCC spike-in RNAs were amplified to their spiked-in copy numbers during the initial cDNA amplification (FIG. 7B). The number of genes expressed by mESC is consistent with the amount of initially amplified cDNA. In addition, it was shown that the content of gene is maintained during amplification of cDNA and SC3-seq library construction step.

FIG. 1D shows the averaged sequence read distribution of one of the amplified products of the 100 ng RNAs by the SC3-seq (~40-50% mapping efficiency). In agreement with the design of SC3-seq, the mapped reads were highly enriched at the 3' ends (150 bp upstream from the TTSs) of all mapped RefSeq genes. Low enrichment of the mapped reads was found on the anti-sense strands of exons, which represents amplification products in which the V1 (dT)24 primer was mis-annealed to the 5' ends of cDNAs for amplification (FIG. 1C). For example, the SC3-seq track around the Pou5f1 locus exhibited a single clear peak corresponding to the 3' end of the sense strand of Pou5f1, with several minor peaks on the anti-sense strand of the exons (FIG. 1E). For a fraction of genes, the peaks of the SC3-seq reads were observed downstream of the 3' ends of annotated RefSeq transcripts, suggesting that these loci correspond to the 3' ends of the upstream transcripts (FIGS. 1D and 1E). For example, for the Nanog locus, the SC3-seq peaks were observed 1 kb downstream of the annotated 3' end of Nanog (FIG. 1E). In fact, the published comprehensive RNA-seq data of mESC identifies the same peak contiguous to the peaks of the upstream exons of Nanog (FIG. 1E) (Anders, S, et al., Bioinformatics, 31, 166-169, 2015), indicating that the 3' end peaks detected by the SC3-seq are a part of Nanog transcripts. From the above, it was suggested that the 3' ends of a fraction of the RefSeq transcripts can be re-defined in SC3-seq. The correlation between the in silico extension of the TTSs of the RefSeq transcripts and the gene numbers that showed an increase in the mapped reads by SC3-seq was examined.

As shown in FIG. 1F, the number of genes that exhibited the increase of mapped reads increased by the extension of the definition of the TTSs from the annotated TTSs, and 450 genes exhibited the increase of their mapped reads by the extension of the definition of the TTSs by 10 kb. Since expansion by more than 10 Kb was found to cause erroneous annotation, a peak detected within 10 Kb downstream from the annotated TTS showing the expression of proximate upstream gene was defined, and the data of SC3-seq was analyzed. The stability of comprehensive RNA amount of mESC based on this definition was confirmed by analyzing the published RNA-seq data.

EXAMPLE 3

Evaluation of the Qantitativity of SC3-Seq

Figure 2:
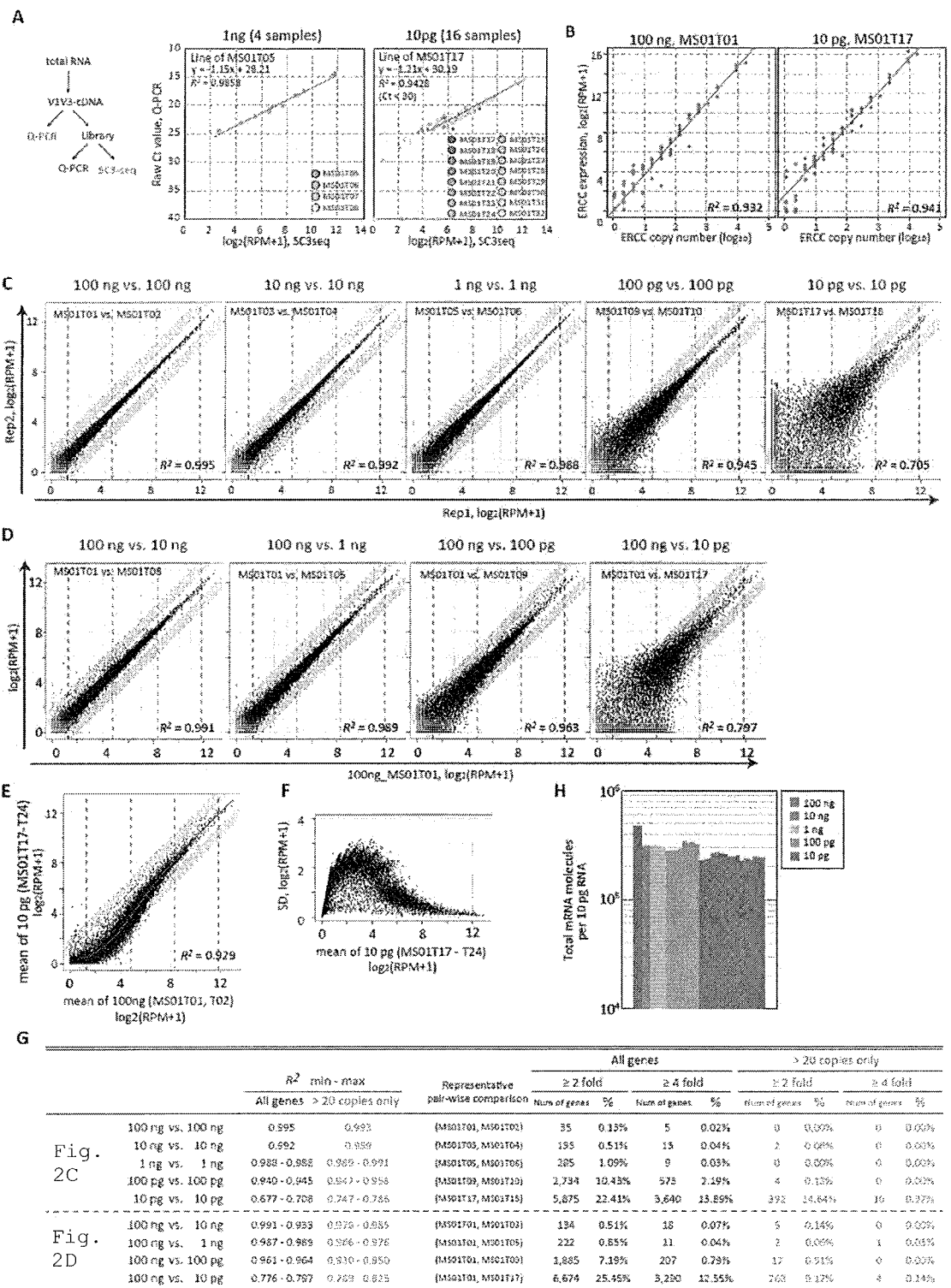
FIG. 2A is a graph showing comparison of the expression levels of the cDNAs amplified by Q-PCR [from 1 ng (middle) and 10 pg (right) total RNAs, prior to the SC3-seq library construction] (Ct value) with those estimated by the SC3-seq [log$_2$ (RPM+1)]. The left Figure shows the concept of comparison method.
FIG. 2B is a graph showing correlations between the quantities of the ERCC RNAs in a dilution series of mESC total RNAs (MS01T01 and MS01T17 for 100 ng and 10 pg of total RNAs, respectively) and SC3-seq [log$_2$ (RPM+1)] by SC3-seq [log$_2$ (RPM+1)]. The SC3-seq data for the ERCC spike-in RNAs with not less than 10 copies per 10 pg were used for the regression line.
FIG. 2C is a scatter diagram showing comparison between two independently amplified replicates from 100 ng, 10 ng, 1 ng, 100 pg and 10 pg of mESC total RNAs. In the Figure, the white and yellow areas indicate expression-level ranges within 2-fold and 4-fold differences. In the Figure, copy numbers per 10 pg of total RNAs estimated by the SC3-seq reads of the ERCC spike-in RNAs in 100 ng of RNAs are indicated by dashed lines (vertical lines) (1000 copies, 100 copies, 10 copies and 1 copy from the right).
FIG. 2D is a scatter diagram showing comparison between replicates from 100 ng of total RNAs and a replicate from 10 ng, 1 ng, 100 pg and 10 pg of mESC total RNAs. In the Figure, the white and yellow areas indicate expression-level ranges within 2-fold and 4-fold differences. In the Figure, copy numbers per 10 pg of total RNAs estimated by the SC3-seq reads of the ERCC spike-in RNAs in 100 ng of RNAs are indicated by dashed lines (vertical lines) (1000 copies, 100 copies, 10 copies and 1 copy from the right).
FIG. 2E is a scatter diagram showing comparison between averaged SC3-seq data [log$_2$ (RPM+1)] of 100 ng of mESC total RNAs with those of 10 pg of total RNAs. In the Figure, the white and yellow areas indicate expression-level ranges within 2-fold and 4-fold differences, respectively. In the Figure, copy numbers per 10 pg of total RNAs estimated by the SC3-seq reads of the ERCC spike-in RNAs in 100 ng of RNAs are indicated by dashed lines (vertical lines) (1000 copies, 100 copies, 10 copies and 1 copy from the right).
FIG. 2F is a graph plotting standard deviations of gene expression levels against gene expression levels by the SC3-seq in eight 10 pg RNA samples.
FIG. 2G shows the relationship between comparisons of minimum (min) and maximum (max) correlation coefficients ($R^2$) and percentages of genes within 2- and 4-fold expression differences (all gene expressions and genes that expressed not less than 20 copies per 10 pg).
FIG. 2H is a graph showing total mRNA molecule numbers per 10 pg RNA, which are estimated from the copy numbers of ERCC spike-in RNAs in 100 ng, 10 ng, 1 ng, 100 pg and 10 pg of mESC total RNAs.

To evaluate quantitativity of SC3-seq, the correlation between the threshold-cycle (Ct) values measured by Q-PCR as the number of genes in cDNAs amplified from 1 ng (corresponding to 100 cells) and 10 pg (corresponding to 1 cell) of total RNAs, and the SC3-seq reads [$\log_2$ (RPM+1)] of the same set of genes in the library prepared from the same cDNAs was analyzed. As shown in FIG. 2A, the Ct values and the SC3-seq reads exhibited correlations between the both cDNAs ($R^2$=0.9858 and 0.9428 for cDNAs from 1 ng and 10 pg RNAs, respectively). Furthermore, the SC3-seq read [$\log_e$ (RPM+1)] values of the ERCC spike-in RNAs in all amplified libraries obtained by dilution correlated proportionally to their original copy numbers (FIG. 2B) (copy numbers of ERCC spike-in RNAs per 10 pg total RNAs at each dilution are shown), although the spike RNAs that provided not more than 30 copies in 10 pg RNAs exhibited insufficient amplification. This makes it possible to estimate the copy number per 10 pg RNAs of a gene from its SC3-seq read number. The scatter-plot analyses indicated that samples amplified from 100 ng (corresponding to 10,000 cells), 10 ng (corresponding to 1,000 cells) and 1 ng (corresponding to 100 cells) RNAs exhibited excellent correlations ($R^2$=0.994, 0.992, 0.988, respectively), with all the genes plotted within the 2-fold difference lines (FIGS. 2C and 2G). The samples amplified from 100 pg (corresponding to 10 cells) RNAs also showed very good correlations, with 89.6 and 97.8% of genes plotted within the 2- and 4-fold difference lines, respectively (FIGS. 2C and 2G). The samples amplified from 10 pg (corresponding to 1 cell) RNAs exhibited good correlations, with 77.6 and 86.1% of genes plotted within the 2- and 4-fold difference lines, respectively (FIGS. 2C and 2G). Amplified samples showed better correlations for genes that are expressed more than 20 copies per 10 pg of RNAs, and particularly for those amplified from 10 pg of RNAs, with $R^2$=0.764, with 85.4 and 99.6% of genes plotted within the 2- and 4-fold difference lines, respectively (FIGS. 2C and 2G).

When compared to the sequence profiles of samples amplified from 100 ng (corresponding to 10,000 cells) of RNAs, samples amplified from 10 ng (corresponding to 1,000 cells), 1 ng (corresponding to 100 cells) and 100 pg (corresponding to 10 cells) of RNAs exhibited good correlations ($R^2$=0.991, 0.989 and 0.963, respectively), and those amplified from 10 pg (corresponding to 1 cell) RNAs showed good correlations ($R^2$=0.797), with 75 and 87% of genes plotted within the 2- and 4-fold difference lines, respectively (FIGS. 2D and 2G). For genes that are expressed in more than 20 copies per 10 pg of RNAs, samples amplified from 10 pg (corresponding to 1 cell) RNAs showed good correlations ($R^2$=0.813), with 90.8 and 99.9% of genes plotted within the 2- and 4-fold difference lines, respectively (FIGS. 2D and 2G).

To evaluate the SC3-seq for single cell level RNAs, the log-averaged expression levels in two samples amplified from 100 ng of RNAs with those in eight samples amplified from 10 pg of RNAs were compared. The scatter-plot analysis showed that the averaged samples exhibited a good correlation ($R^2$=0.939), with 79.8 and 97% of genes (all expression ranges) plotted within the 2- and 4-fold difference lines (FIG. 2E to 2G). For genes that are expressed in more than 20 copies per 10 pg of RNAs, they showed a good correlation ($R^2$=0.930), with 98.6 and not less than 99.9% of genes plotted within the 2- and 4-fold difference lines, respectively (FIG. 2E to 2G). Collectively, these findings demonstrate the very highly quantitativity of the SC3-seq for RNAs ranging from 100 ng (corresponding to 10,000 cells) to 10 pg (corresponding to 1 cell). Based on these results, the number of mRNA molecules present in 10 pg (corresponding to 1 cell) of mESC total RNAs was estimated to be about 300,000, a value in good agreement with previous findings (FIG. 2H).

To examine the SC3-seq, the coverage [number of genes detected in 10 pg RNAs ($\log_2$ (RPM+1)≥1/number of genes detected in 100 ng RNAs ($\log_2$ (RPM+1)≥1] and accuracy [number of genes detected in 10 pg RNAs ($\log_2$ (RPM+1) ≥1) that are detected in 100 ng RNAs ($\log_2$ (RPM+1)≥1)] of SC3-seq from 10 pg RNAs by using the data from 8 replicates were further evaluated.

Figure 3:
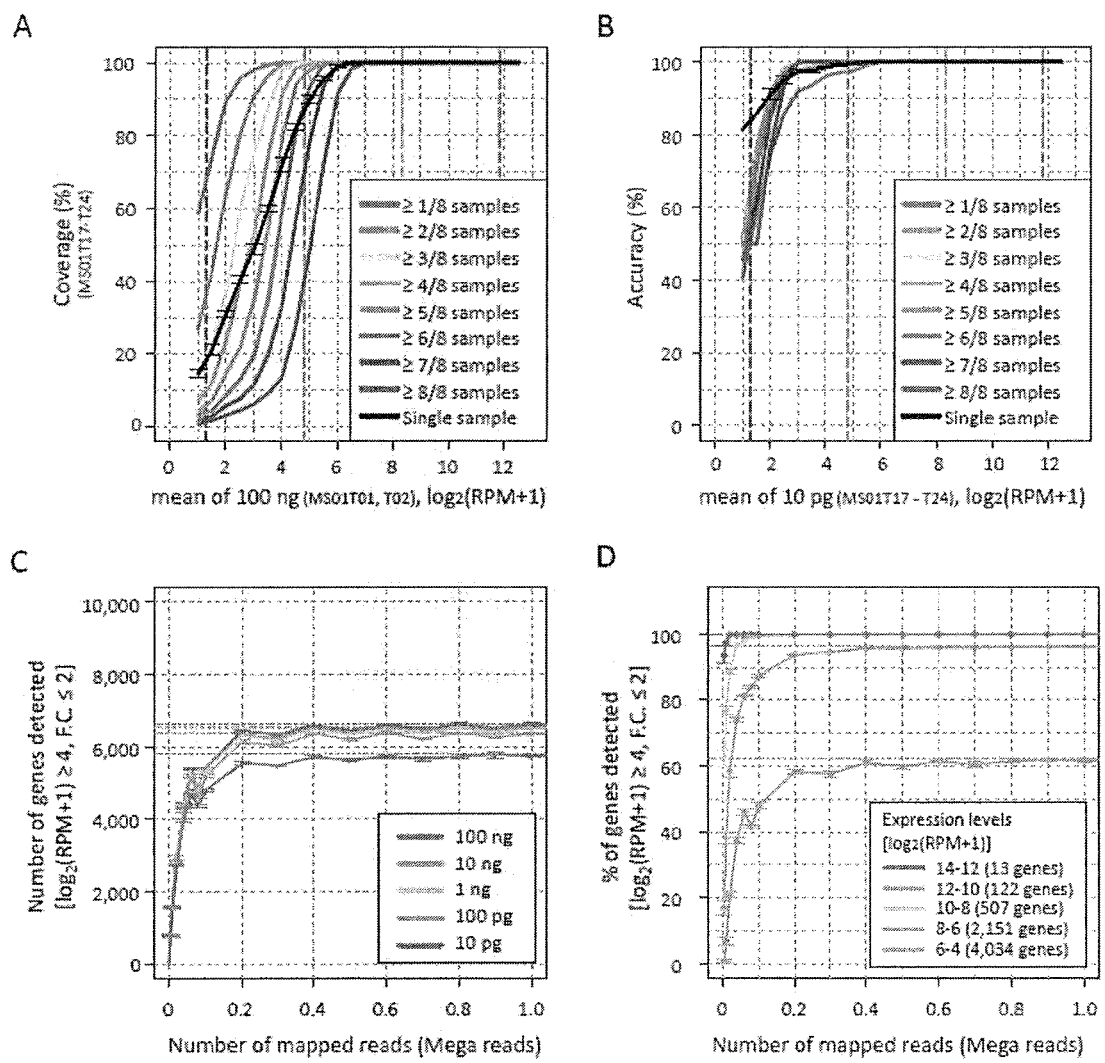
FIG. 3A is a graph showing coverage of SC3-seq from 10 pg of total RNAs as a function of the expression level [log$_2$ (RPM+1)] in 100 ng of total RNAs. The black lines represent the means of coverage in single-sample analysis. The results of multiple-sample analyses under the detection definition of transcripts detected in ≥1-8 of eight amplified samples are respectively shown. In the Figure, copy numbers per 10 pg of total RNAs, which is calculated by SC3-seq reads of ERCC spike-in RNAs in 100 ng of RNAs are indicated by dashed lines (vertical lines) (1,000 copies, 100 copies, 10 copies, 1 copy from the right).
FIG. 3B shows accuracy of the SC3-seq from 10 pg of total RNAs as a function of the expression level [log$_2$ (RPM+1)]. The black lines represent the means of accuracy of single-sample analysis. The results of multiple-sample analyses under the definitions of detection where transcripts are detected in 1-8 of the eight amplified samples are shown. In the Figure, copy numbers per 10 pg of total RNAs estimated by the SC3-seq reads of the ERCC spike-in RNAs in 100 ng of RNAs are indicated by dashed lines (vertical lines) (1000 copies, 100 copies, 10 copies, 1 copy from the right).
FIG. 3C is a graph showing the plot of the number of genes [log$_2$ (RPM+1)≥4, ≤2-fold compared to gene expression level determined by full length reads] by SC3-seq from 100 ng, 10 ng, 1 ng, 100 pg and 10 pg of mESC total RNAs as a function of the reads.
FIG. 3D is a graph showing the plot of the percentage [≤2-fold compared to gene expression level determined by full length reads] by SC3-seq from 10 pg of mESC total RNAs as a function of reads, which is categorized by expression level ranges in 100 ng of total RNAs.

The expressed genes were defined as those that were detected [$\log_2$ (RPM+1)≥1] in samples prepared by SC3-seq from 100 ng of RNAs. Coverage of the single amplified samples as a function of the expression level was plotted (black lines in FIG. 3A). As expected from the previous reports and the data shown above (FIG. 2), coverage was dependent on the expression level, but a vast majority of the expressed genes (cumulative percentage, 94.1%) that are expressed more than 10 copies per 10 pg RNAs were successfully detected (FIG. 3A). The accuracy of the single amplified samples was plotted similarly, and it was confirmed that 99.7% (cumulative percentage) of the genes detected were expressed in the expression level range of more than 10 copies per 10 pg RNAs (FIG. 3B). When multiple sample analyses (8 samples) were performed, coverage was improved under the definitions of detection where 1 to 5 of the 8 amplified samples exhibited reads (not less than 10 copies per 10 pg RNAs), whereas accuracy was nearly 100% under all detection definitions (FIGS. 3A and 3B). These findings indicate that a single sample prepared by SC3-seq from single-cell level RNAs has excellent coverage and accuracy, and multiple sample analyses also showed improved coverage and improved accuracy.

An advantage of SC3-seq is that it allows for high quantification of gene expression with a relatively small number of sequence reads. Successively, the number of reads capable of determining gene-expression levels of 100 ng (corresponding to 10,000 cells) to 10 pg (corresponding to 1 cell) of RNAs was examined. The number of genes was plotted under the condition of $\log_2$ (RPM+1)≥4 (not less than 5 copies per 10 pg RNAs) and the read numbers were detected. As shown in FIG. 3C, the number of genes detected under the condition of [$\log_2$ (RPM+1)≥4] with 100 ng (corresponding to 10,000 cells) to 10 pg (corresponding to 1 cell) of RNAs prepared by SC3-seq was around 0.2 mega mapped reads as the upper limit wherein the detected gene number was almost constant (up to 7000) in RNAs of from 100 ng (corresponding to 10,000 cells) to 100 pg (corresponding to 10 cells), and similar (up to 6000) in 10 pg RNAs (corresponding to 1 cell). Then, the percentage of genes detected by SC3-seq from 10 pg of RNAs, among the genes detected from 100 ng of RNAs against the sequence reads, was plotted for each range of the expression level (FIG. 3D). It was confirmed from the analyses that nearly 100% of genes under the condition of $\log_2$ (RPM+1)≥6 (not less than 20 copies per 10 pg RNAs) and around 60% of genes under the condition of $\log_2$ (RPM+1)≥4 (not less than 5 copies per 10 pg RNAs) were detected as the upper limit of about 0.2 mega mapped reads (FIG. 3D). It was found that, to identify genes expressed at a substantial level [$\log_2$ (RPM+1)≥4 not less than 5 copies per 10 pg RNAs] by SC3-seq, it is sufficient to perform 0.2 mega mapped reads per sample, and that a small number capable of parallel sequencing of numerous samples is sufficient.

EXAMPLE 4

Comparison of Function of SC3-Seq with that of Other Methods

To compare quantitative function of SC3-seq, it was compared with other methods for single cell RNA-seq. First, the relationship between the expression level and the transcript length in samples prepared by the SC3-seq and other methods, as a control, was examined. Furthermore, it was also compared with the published RNA-seq prepared from an exhaustive quantity of RNAs of mESCs and MEFs. As shown in FIG. 4A, the control samples exhibited a highly diverse distribution of expression-level ranges irrespective of the transcript lengths and cell types (Ohta_mESCs and Ohta_MEFs), and the average expression levels were similar among all transcript lengths [the modes of expression levels are $\log_2$ FPKM (fragment per kilobase per million mapped reads)=2]. Remarkably, the distribution of the expression-level ranges as a function of the transcript length detected in mESCs by the SC3-seq for 100 ng and 10 pg of RNAs was similar to that by the control RNA-seq (FIG. 4A). For example, the modes of the expression levels are similar (around $\log_2$ RPM=4) with any length of the transcript, and so is the expression level of genes with any length of the transcript. The results indicate that SC3-seq shows gene expression of a transcription product of any length, even when a single cell level is used as the initial material.

On the other hand, the results of Yan et al. for single human ESC (full-length RNA-seq amplification method, Tang, F., et al, Nat Methods, 6, 377-382, 2009, Tang, F., et al, Nature protocols, 5, 516-535, 2010 and Ohta, S. et al., Cell reports, 5, 357-366, 2013) and report of Picelli et al. on single MEF (SMART-seq 2, Picelli, S., et al, Nat Methods, 10, 1096-1098, 2013) show the same tendency. Since the mode of expression level depends on the length of the transcription product, due to the low efficiency of the synthesis and amplification of long transcription products (e.g., the mode of expression level of a longer gene is low and that of a shorter gene is high), the results are different from those of SC3-seq and control RNA-seq (FIG. 4A).

A difference in the read position in the transcripts by SC3-seq and other single-cell RNA-seq methods was examined. As shown in FIGS. 4B and 4C, the SC3-seq exhibited a clear sharp peak exclusively at the 3' ends of the transcripts across all the transcript length ranges, as described in FIG. 1. On the other hand, in other methods, non-uniformity was revealed depending on the length of the transcription product, and particularly, a distorted read was found in the 3'-terminal of a long transcription product (FIG. 4C).

From these results, SC3-seq requires 0.2 mega mapped reads for short transcription products (<500 bp) (gene with gene expression level of not less than the 6,555th from the top (¼ of annotated transcription product in mouse), $\log_2$ RPM≥3.69±0.05), and other methods require not less than 1 mega mapped reads for short transcription products (<500 bp) (less than 500 bp, gene with gene expression level of not less than the 6,555th and not less than 6,217th from the top (each ¼ of annotated transcription products in mouse and human), $\log_2$ FPKM≥2.21±0.05 (Yan et al.) or 2.92±0.27 (Picelli et al.)) (FIG. 4D). From the above, it was suggested that SC3-seq is a more quantitative and effective method in single cell transcriptome analysis, as compared to conventional methods.

EXAMPLE 5

Gene Analysis of Difference of Cell Type in Pre-Implantation Mouse Embryo

The pre-implantation mouse blastocysts at embryonic day (E) 4.5 consist of at least three distinct cell types: the epiblasts, the primitive endoderm (PE) and the trophectoderm (TE). The former two cell types make up the ICM. Based on the anatomical location, the TE can be classified into two types: the pTE (polar TE), which directly contacts the ICM and subsequently forms extra-embryonic ectoderm (ExE), and the mTE (mural TE), which is located at the abembryonic tissue part of the blastocysts and later forms primary trophoblast giant cells. There has been no report exploring whether gene-expression differences exist between pTE and mTE at E4.5. Thus, whether the SC3-seq successfully discriminates cell-type differences in the blastocysts was determined.

Figure 5:
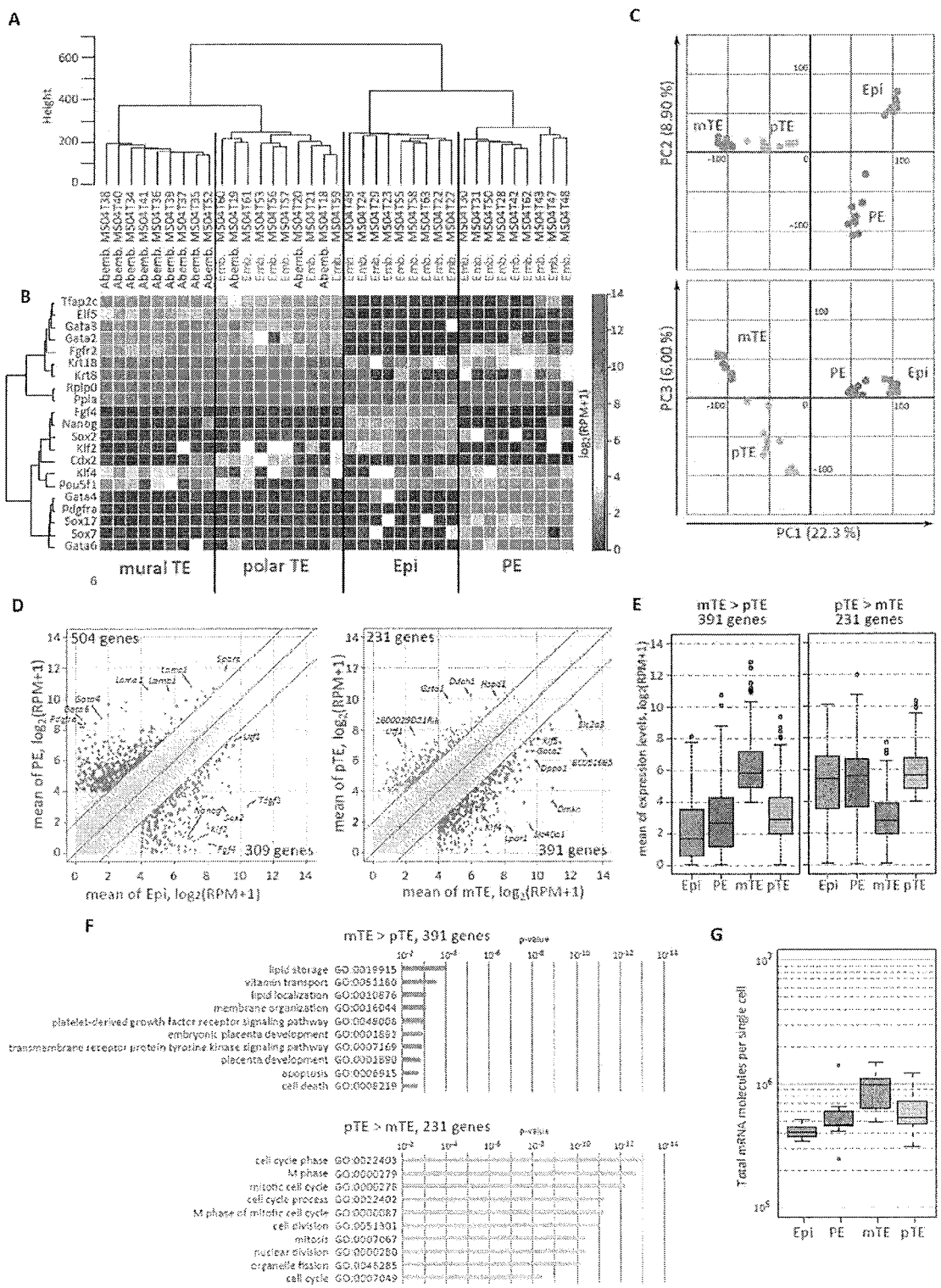
FIGS. 5A and 5B show unsupervised hierarchical clustering (UHC) with all expressed genes [$\log_2$ (RPM+1)≥4 in all samples, 12,010 genes] (FIG. 5A) and a heat map of the expression levels of marker genes for epiblast, primitive endoderm (PE) and trophectoderm (TE) (FIG. 5B). The annotated cell types [epiblast, PE, polar TE and mural TE] were defined based on the clustering, locations and expression of known marker genes.
FIG. 5C shows the results of principal component analysis (PCA) of the cells by all expressed genes. They are shown in the drawings developed with PC1 and PC2 (top) or PC1 and PC3 (bottom).
FIG. 5D is a graph plotting differences in the average gene expression between epiblast (nine samples) and PE (nine samples) (left), and between mTE (nine samples) and pTE (10 samples) (right). The difference in the gene expression shows not less than 4-fold difference in one cell type with mean $\log_2$ (RPM+1)≥4. The genes showing up-regulated expression in PE (504 genes), epiblast (309 genes), pTE (231 genes) and mTE (391 genes) are colored blue, green, yellow and orange, respectively.
FIG. 5E is a graph showing expression of the genes showing up-regulated expression in mTE (left) or pTE (right) among the four cell types. The bar in the box indicates the average expression level.
FIG. 5F shows the results of gene ontology (GO) analysis of genes showing up-regulated expression in mTE (top) or pTE (bottom).
FIG. 5G shows average gene expression levels in the four cell types, which were calculated based on the copy numbers of ERCC spike-in RNAs. The bar in the middle of the box indicates the average expression level.

Pre-implantation blastocysts at E4.5 were isolated (FIG. 11A), bisected into embryonic and ab-embryonic parts, dissociated into single cells, and single cells considered to compose mTE or pTE/ICM were picked up and cDNAs thereof were amplified. The amplification efficiency of cDNAs was examined by analyzing the expression level of Gapdh and the ERCC spike-in RNAs (FIGS. 11B and 11C), the cDNAs were roughly classified by analyzing the expression of the key markers Nanog (epiblast), Gata4 (PE), Cdx2 (TE) and Gata2 (TE) (FIG. 11B), and among 67 single-cell cDNAs, 37 representative cDNAs [12 for mTE, 8 for m/pTE, 9 for epiblasts, 9 for PE by their anatomical location and marker expression; it was noted that the Gata2-positive TE lacked Cdx2 mRNA expression at this stage, although all the TE showed CDX2 by immunofluorescent staining (FIGS. 11A and 11B)] by the SC3-seq analysis. Unsupervised hierarchical clustering (UHC) revealed that these cells are classified largely into two clusters, both of which are further divided into two sub-clusters (FIG. 5A). The one cluster consists of two sub-clusters representing, based on the expression of key marker genes, the epiblasts and the PE (Fgf4, Nanog, Sox2 and Klf2 for the epiblasts and Gata4, Pdgfra, Sox17, Sox7 and Gata6 for the PE) (FIG. 5A). Among the cells in the other cluster, 9 out of 12 mTE (cells isolated from the ab-embryonic tissue) were classified into one sub-cluster and the remaining three were classified into the neighboring sub-cluster having pTE confirmed by a marker and an anatomical location. In the principle component analysis (PCA) by UHC analysis, they were classified into four groups (FIG. 5C). These findings successfully demonstrate that the SC3-seq successfully identifies the distinct cell types in developing embryos and that mTE and pTE exhibit differential gene expression as a whole at E4.5.

Figure 11:
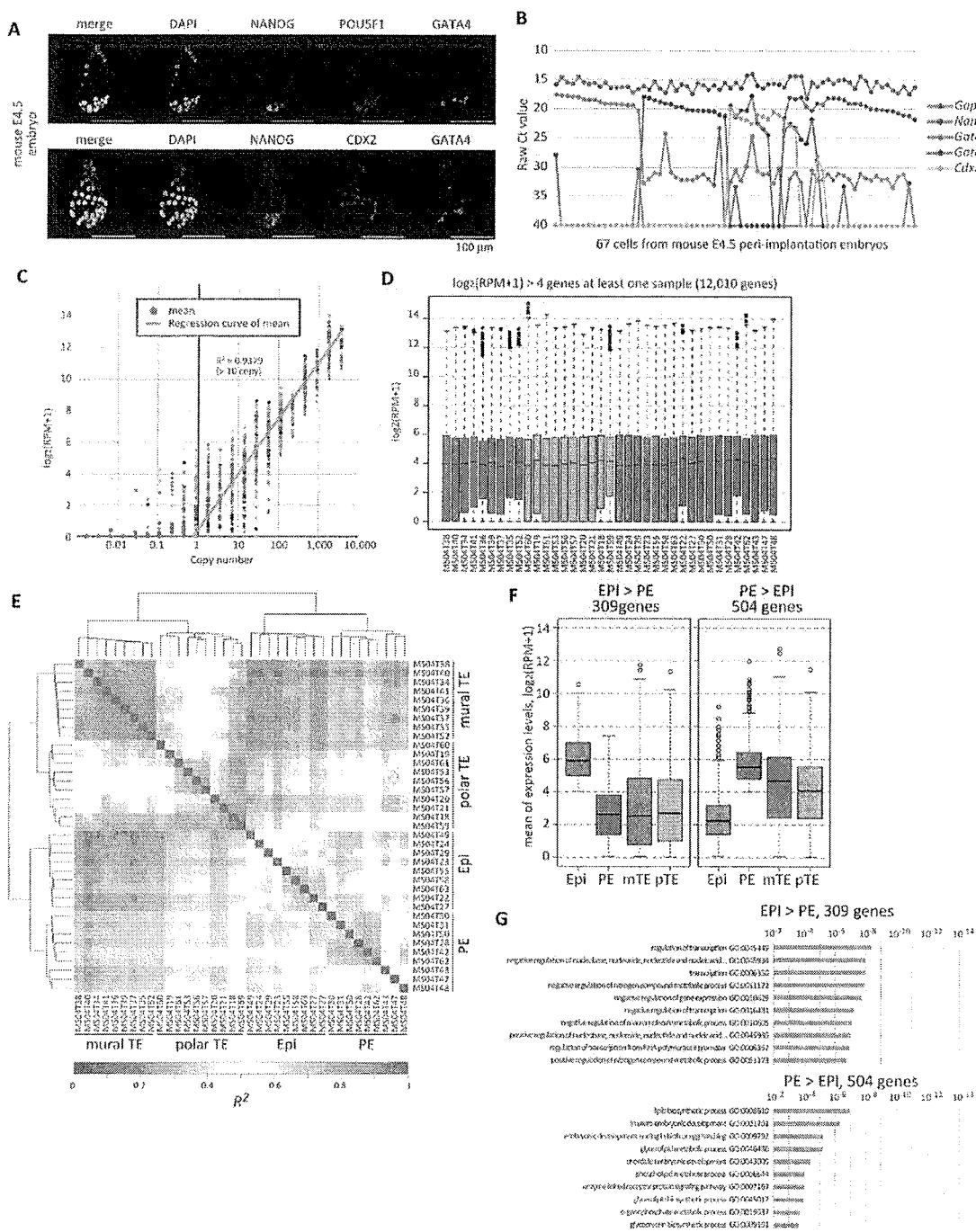
FIG. 11A shows the results of immunofluorescence analysis of expression of marker genes [NANOG (epiblasts), POU5F1 (epiblasts and PE), GATA4 (PE), and CDX2 (TE)] in pre-implantation embryos on day E4.5. The scale bar was 100 μm.
FIG. 11B shows the results of Q-PCR analysis of expression of marker genes [NANOG (epiblasts), GATA4 (PE), CDX2 (TE), Gapdh (housekeeping)] in amplified cDNAs (quality-checked 67 cDNAs) from single cells of pre-implantation embryos on day E4.5.
FIG. 11C shows scatter-plot comparison of ERCC spike-in RNA in amplified samples measured by SC3-seq [$\log_2$ (RPM+1)] with the original copy number. The regression curve and correlation coefficient were calculated from the mean of probes whose copy numbers are not less than 10.
FIG. 11D shows the results of box-plot of distribution of gene expression level in each cell.
FIG. 11E shows a heat-map of the correlation coefficients ($R^2$) among all embryonic cells.
FIG. 11F shows the results of the box-plot of expression levels of genes showing up-regulated expression in epiblasts compared to PE (left) and genes showing up-regulated expression in PE compared to epiblasts (right).
FIG. 11G shows the results of GO analysis of genes showing up-regulated expression in epiblasts compared to PE (top) or genes showing up-regulated expression in PE compared to epiblasts (bottom).

To further evaluate the SC3-seq, genes that are differentially expressed between the epiblasts and the PE were found [defined as different genes in their average expression levels of 4-fold, $\log_e$ values (RPM+1) of ≥4 and FDR of <0.01 based on oneway analysis of variance (ANOVA)]. Consistent with previous findings, genes up-regulated in the epiblasts (313 genes) included Tdgf1, Utf1, Sox2 and Nanog and were enriched with ontology (GO) term such as 'regulation of transcription', 'negative regulation of gene expression' and 'negative regulation of macromolecule metabolic process', whereas genes up-regulated in the PE (502 genes) included Sparc, Lama1, Lamb1, Col4a1, Gata4, Gata6, Pdgfra and Sox17, and were enriched with GO terms such as 'lipid biosynthetic process', 'glycerolipid metabolic process' and 'embryonic development in birth or egg hatching' (FIG. 5D and FIG. 11).

The genes that are differentially expressed between pTE and mTE were examined. 218 Genes that are up-regulated in pTE, which include Hspd1, Ddah1, Gsto1 and Dnmt3b, and are enriched with cell cycle-related GO terms such as 'cell cycle', 'M phase' and 'mitotic telophase' (FIGS. 5D and 5F) were identified. It was confirmed that the genes up-regulated in pTE in comparison to mTE were expressed in the epiblasts and the PE at similar levels to that in pTE (FIG. 5E), indicating that these genes are specifically down-regulated in mTE in the blastocysts. On the other hand, 392 genes were found that are up-regulated in mTE, which include Slc2a3, Basp1, Klf5, Gata2 and Dppa1, and are enriched with GO terms such as 'vitamin transport', 'PDGFR signaling pathway', 'lipid storage', 'embryonic placenta development' and 'membrane organization' (FIGS. 5D and 5F). These data shows good agreement with the idea that mTE stops or slows down the mitotic cell cycle at E4.5 and takes on an end-replication pathway for differentiation into primary trophoblast giant cells.

The average copy number of a gene that expresses not less than 100 copies per each cell type was calculated, and it was found that single mTE cells bear more abundant transcripts (around 2-fold) than single epiblast cells, PE cells and pTE cells (FIG. 5G). This further supports the idea that mTE is an end-replicate bearing a larger amount of transcripts compared to typical single cells at this embryonic stage. Thus, when used together with the ERCC spike-in RNAs, the SC3-seq allows a quantification of transcript in single cells.

EXAMPLE 6

Detection of heterogeneity of human iPS cells

Figure 6:
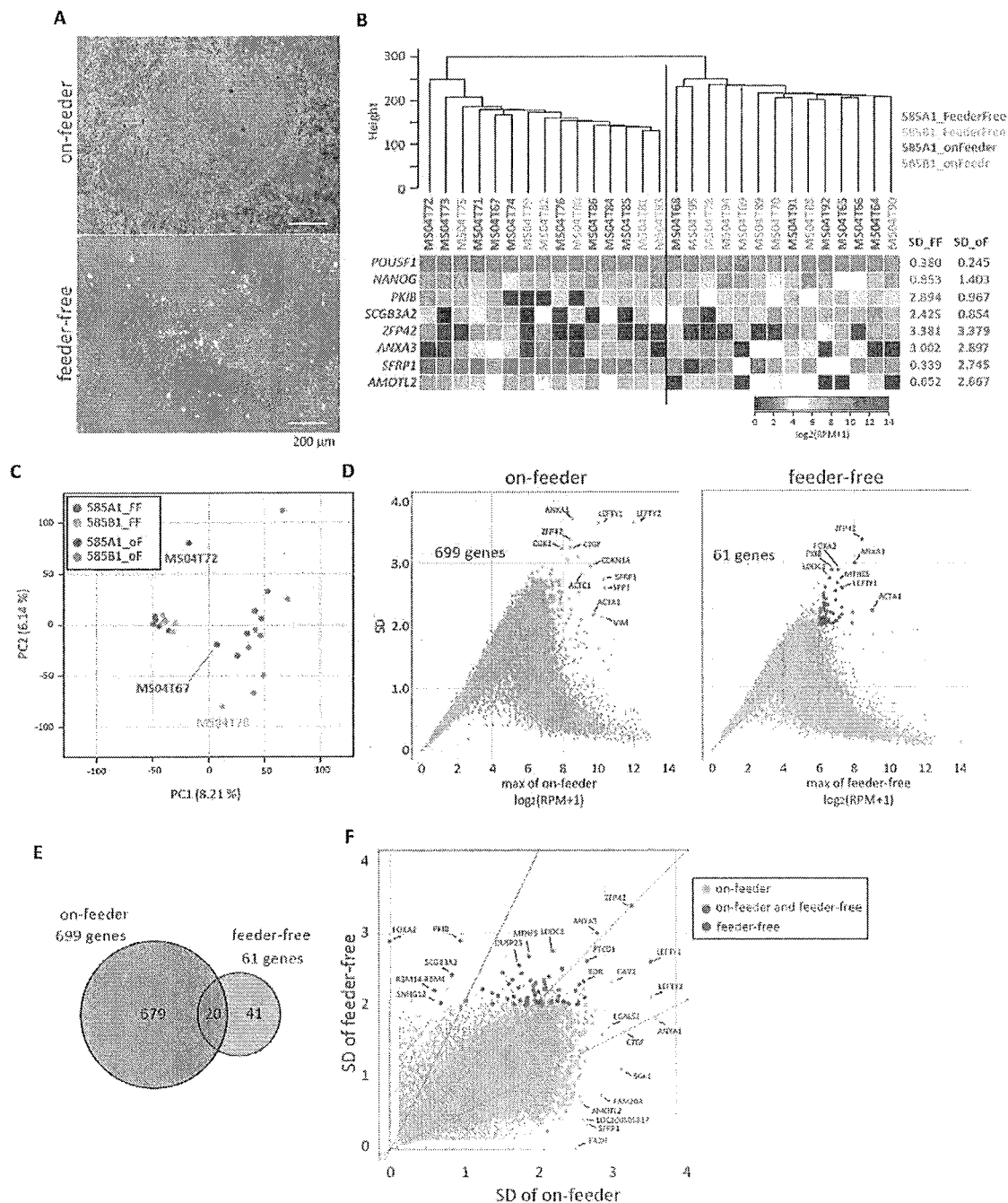
FIG. 6A is a graph showing phase-contrast images of the hiPSC colonies (585B1) cultured with the SNL feeder cells (top) or without feeder free cells (bottom).
FIG. 6B shows the results of UHC with all expressed genes [$\log_2$ (RPM+1)≥4 in all samples, 12,406 genes] and heat map representation of the gene expression levels.
FIG. 6C shows the results of PCA of all cells by all expressed genes. The cells are plotted by PC1 and PC2.
FIG. 6D is a graph plotting gene expression of hiPSCs on feeder cells (left) and under feeder-free conditions (right) by plotting the maximum expression level of each group (MS04T72, MS04T67 and MS04T78, as shown in FIG. 6C) against standard deviations (SDs). Genes that show the max expression level≥6 and SD≥2 are considered to be highly heterogeneously expressed genes [699 genes in on-feeder hiPSCs and 61 genes in feeder-free hiPSCs].
FIG. 6E is a Venn diagram showing the relationship among the heterogeneously expressed genes in FIG. 6D.
FIG. 6F is a graph showing plot of the SDs of gene expression levels in hiPSCs cultured on-feeder cells and in hiPSCs under feeder-free conditions.
Figure 12:
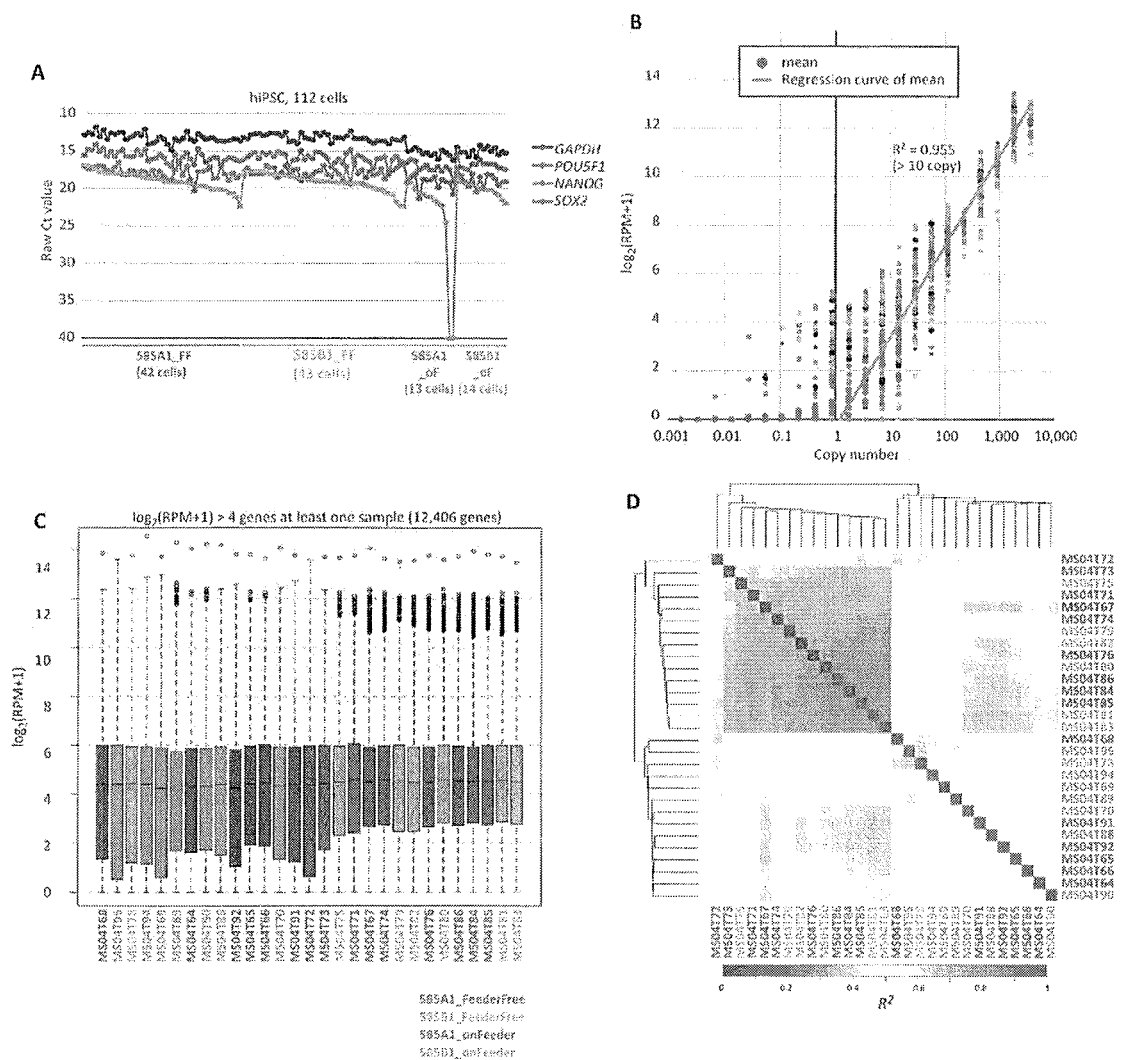
FIG. 12A shows the results of Q-PCR analysis of the expression of pluripotent genes [POU5F1, NANOG, SOX2, and GAPDH (housekeeping)] in amplified cDNAs (112 quality-checked cDNAs) from hiPSCs (585A1 and 585B1) cultured on or without feeder cells.
FIG. 12B shows scatter-plot comparison of ERCC spike-in RNA in amplified samples measured by SC3-seq ($\log_2$ (RPM+1)) with the original copy number. The regression curve and correlation coefficient were calculated from the mean of probes whose copy numbers are not less than 10.
FIG. 12C shows the results of box-plot of distribution of gene expression level in each cell.
FIG. 12D shows a heat-map of the correlation coefficients ($R^2$) among all embryonic cells.

It was next examined whether the SC3-seq successfully detects the heterogeneity of gene expression in homogeneous cell populations. The gene expression of hiPSCs cultured on feeder cells (on-feeder hiPSCs) and in hiPSCs cultured under a feeder-free condition (feeder-free hiPSCs) was measured. For this purpose, two lines of hiPSCs (585A1 and 585B1) were cultured on the SNL feeder cells and cultured under a feeder-free condition (in total we generated 112 single-cell cDNAs) (FIG. 6A and FIGS. 12A and 12B) and an SC3-seq analysis of the cells was performed (7, 7, 8 and 7 single cells for on-feeder 585A1, on-feeder 585B1, feeder-free 585A1 and feeder-free 585B1, respectively) (FIG. 12C). The UHC analysis revealed that the on-feeder hiPSCs and the feeder-free hiPSCs could be classified into two distinct clusters irrespective of the line difference, with the exception that one on-feeder hiPSC was classified into the feeder-free cluster and one feeder-free hiPSC was classified into the on-feeder cluster (FIG. 6B). This indicated the distinct, although still very similar, the on-feeder and feeder-free hiPSCs. Then, the PCA analysis result showed that the feeder-free hiPSCs, except the two outliers, were clustered tightly together, whereas the on-feeder hiPSCs were more scattered, along the PC2 axis (FIG. 6C), indicating that the gene expression of the on-feeder hiPSCs was more heterogeneous than that of the feeder-free hiPSCs. Further, the standard deviation (SD) of the gene-expression levels was plotted against the gene-expression levels in the on-feeder and feeder-free hiPSCs (FIG. 6D). In on-feeder hiPSC, 630 genes with the maximum expression level $\log_2$ (RPM+1)≥6, SD≥2 were found, and 109 were found by feeder-free hiPSC. That is, in agreement with the results of PCA analysis, in all gene expression regions, it was shown that the SD value of on-feeder hiPSC is higher than the SD value of feeder-free iPSC. The SDs of the gene-expression levels of the feeder-free iPSCs were then plotted against those of the on-feeder hiPSCs and 75 genes with higher SDs were identified in the feeder-free hiPSCs, including PK1B, UNC5D, SCGB3A2, HERC1, RPS4Y1 and RBM14/RBM4, genes with high SDs (SDs≥2) were identified both in the feeder-free and on-feeder hiPSCs, including ZFP42, ANXA3, LEFTY1, PTCD1 and LDOC1, and 596 genes with higher SDs were identified in the on-feeder hiPSCs, including FGF19, CAV1, NODAL, SGK1, CTGF and SFRP1 (FIGS. 6B, 6E and 6F). These findings demonstrate that the feeder-free hiPSCs are more homogeneous in gene expression than the on-feeder hiPSCs. It is suggested that SC3-seq is a powerful method for identifying heterogeneic gene expression in homogeneous cell populations.

EXAMPLE 7

Gene Analysis in Macaca Fascicularis Embryo Pre- and Post-Implantation

Figure 13:
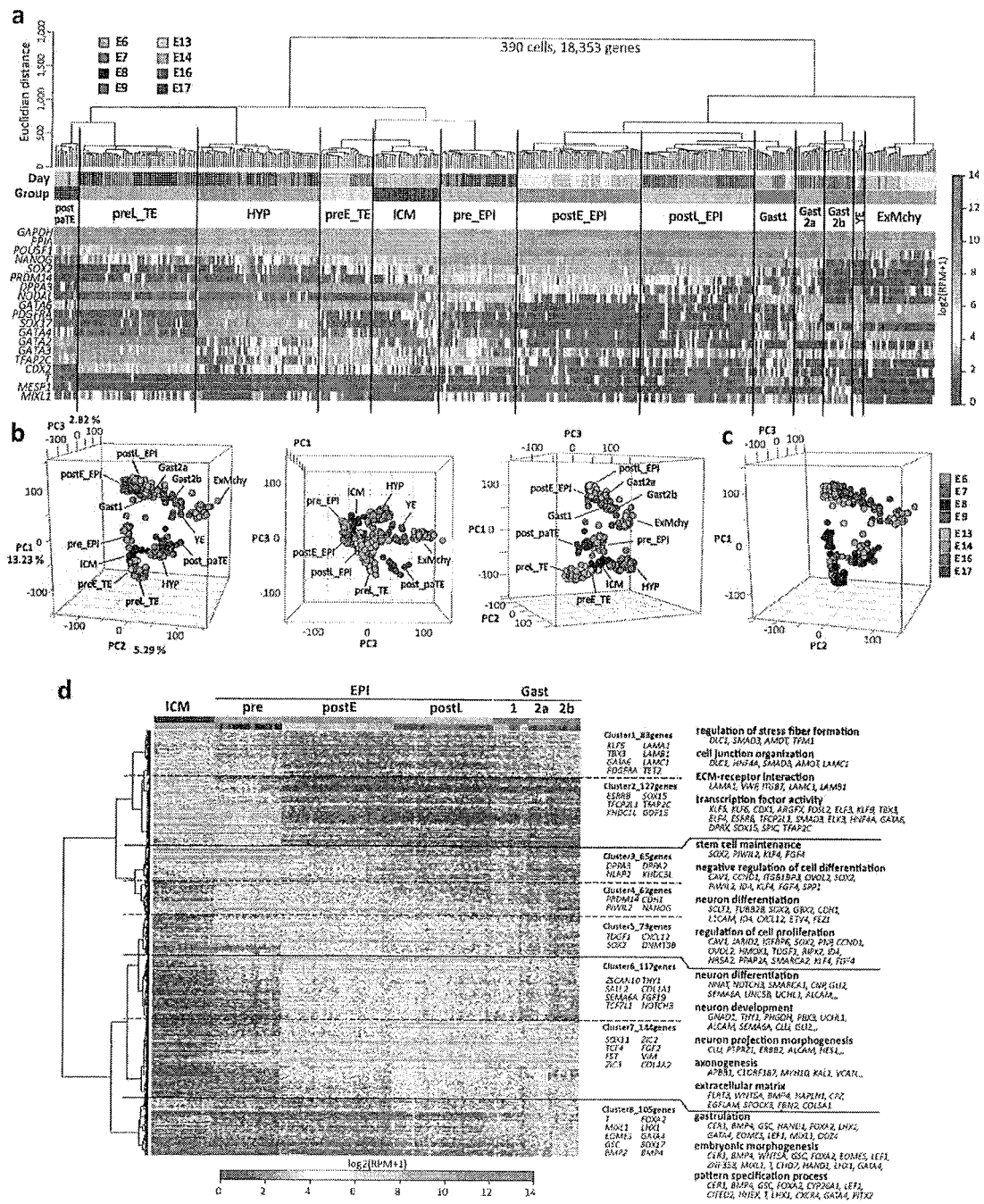
FIG. 13A shows analysis results of expressed gene obtained using SC3-seq from Macaca fascicularis embryo pre- and post-implantation. Expression levels of UHC with all expressed genes (in all samples, $\log_2$ (RPM+1)≥4, 18,353 genes) and a heat-map of the levels of pluripotent cell marker, primitive endoderm marker, differentiation marker associated with gastrulation are shown.
FIG. 13B, C show the results of PCA of all cells by all expressed genes.
FIG. 13D shows a heat-map of the expression level of gene showing radical variation in the expression in the development of intraembryonic cells in the body. The right shows representative genes contained in the cluster, and the results of Gene Ontology analysis.

The transcriptome of 390 representative cells from pre- and post-implantation embryos (pre: 193 cells; post: 197 cells), encompassing all the relevant lineages and their precursors, was examined by the SC3-seq method. UHC classifies all cells into two large clusters; one consisting mainly of pre-implantation cells with at least 6 distinct clusters and the other consisting of post-implantation cells with at least 7 distinct clusters (FIG. 13a). Each cell was defined and classified according to the clusters by UHC, pluripotent cell marker, primitive endoderm marker, and expression pattern of differentiation marker gene associated with gastrulation (post paTE: parietal trophectoderm derived from post-implantation embryo; preL_TE: late trophectoderm derived from pre-implantation embryo; HYP: hypoblast derived from pre-implantation embryo; preE_TE: early trophectoderm cells derived from pre-implantation embryo; ICM: inner cell mass derived from pre-implantation embryo; pre_EPI: epiblast derived from pre-implantation embryo; postE_EPI: early epiblast derived from post-implantation embryo; postL_EPI: late epiblast derived from post-implantation embryo; Gast1, 2a, 2b: gastrulating cells derived from post-implantation embryo; YE: yolk sacendoderm derived from post-implantation embryo; ExMchy: extra-embryonic mesenchyme derived from post-implantation embryo. FIG. 13B, C show the results of PCA of all cells by all expressed genes. FIG. 13D shows a heat-map of the expression level of gene showing radical variation in the expression in the development of intraembryonic cells in the body. From the above, it was found that the cells in the same group show a similar gene expression pattern, which reflects high quantitativity and high reproducibility of SC3-seq. Also, these findings show that SC3-seq successfully distinguish various cell populations and expression patterns thereof in the development of epiblast in Macaca fascicularis.

EXAMPLE 8

Consideration of Aplicability of SC3-Seq Method to Other Next-Generation Sequencer FIG. 14A shows an outline of the construction of a library corresponding to the next-generation sequencer (Miseq, Nextseq500, Hiseq2000/2500/3000/4000) of Illumina, by changing IntV1(dT)$_{24}$ sequence (SEQ ID NO: 4:ctgctgtacggccaaggcgtatatggatccggcgcgccgtcgactttttttt-tttttttt tttttt) in FIG. 1C to Rd2SPV1(dT)$_{20}$ sequence (SEQ ID NO: 14:gtgactggagttcagacgtgtgctcttccgatcatatg-gatccggcgcgccgtcgactttt tttttttttttttttt), and P1-T sequence in FIG. 1C to Rd1SP-T sequence. In 1 ng of RNA extracted from mESC, average SC3-seq track (read density (RPM, ×1,000 reads) was plotted against the position of read from the annotated TTS (transcription termination site) (FIG. 14B). Two independent replicates amplified from 1 ng and 10 pg of total RNA of mESC were analyzed using Miseq of Illumina (FIG. 14C). The sample amplified from 1 ng of total RNA showed very good correlation ($R^2$=0.972). Illumina announced that other next-generation sequencer (Nextseq500, Hiseq2000/2500/3000/4000) can also analyze by using Miseq. In fact, the present inventors also confirmed that analysis is possible with Hiseq2500 (data not shown).

FIG. 15A shows an outline of SC3-seq in the analysis using the above-mentioned Miseq of Illumina, in which V1 (dT)$_{24}$ sequence used for cDNA amplification was changed to P2(dT)$_{24}$ sequence, V3 (dT)$_{24}$ sequence was changed to P1(dT)$_{24}$ sequence, V1(dT)$_{24}$ sequence used for library construction was changed to P2 sequence, N-V3 (dT)$_{24}$ sequence (SEQ ID NO: 5: (NH$_2$)-atatctcgagggcgcgccg-gatccttttttttttttttttttttttttt) was changed to N-P1 sequence (SEQ ID NO: 9: (NH$_2$)-ccactacgcctccgctttcctctctatg), and Rd2SPV1(dT)$_{24}$ sequence was changed to Rd2SP-P2 sequence (SEQ ID NO: 15: gtgactggagttcagacgtgtgctcttcc-gatcctgccccgggttcctcattct). Two independent replicates amplified from 1 ng and 10 pg of total RNA of mESC by utilizing P1(dT)$_{24}$ sequence and P2(dT)$_{24}$ sequence (P1P2 tag) were analyzed using Miseq of Illumina (FIG. 15B). The sample amplified from 1 ng of total RNA showed very good correlation ($R^2$=0.974). cDNAs amplified from 1 ng and 10 pg RNA of total RNA by using V1 (dT)$_{24}$ sequence and V3 (dT)$_{24}$ sequence (V1V3 tag), respectively, and cDNA amplified using P1P2 tag were analyzed using Miseq of Illumina, and the distribution of the expression level of all genes was shown in box plot (FIG. 15C) and of the number of detected genes was shown in a bar graph (FIG. 15D). While the sample amplified using V1V3 tag and P1P2 tag showed a similar pattern, when PIP2 tag was used, somewhat better results were obtained as compared to those using VIV3 tag. From the above, it was shown that SC3-seq is also applicable to analyses using Miseq of Illumina having higher utility, besides SOLiD5500xl of Life Technologies.

The invention claimed is:

1. A method of preparing a nucleic acid population comprising an amplification product maintaining a relative relationship of gene expression level in a biological sample, which method comprising
(a) a step of amplifying a double-stranded DNA comprising a sense strand and an antisense strand, wherein the double-stranded DNA is constituted of (1) any additional nucleic acid sequence X, (2) poly T sequence, (3) cDNA sequence prepared using mRNA sequence isolated from a biological sample as a template, (4) poly A sequence and (5) any additional nucleic acid sequence Yin this order in the orientation from 5' to 3' of the sense strand by using the double-stranded DNA as a template, a first primer comprising any additional nucleic acid sequence X having amine added to the 5'-terminus, and optionally further comprising a poly T sequence at the downstream thereof, and a second primer comprising any additional nucleic acid sequence Y, and optionally further comprising a poly T sequence at the downstream thereof, wherein the additional nucleic acid sequence X is different from the additional nucleic acid sequence Y, such that the first primer cannot hybridize to the 3'-terminus of the sense strand of the double-stranded DNA, (b) a step of fragmenting the double-stranded DNA obtained in step (a), (c) a step of phosphorylating the 5'-termini of the fragmented double-stranded DNA obtained in step (b), (d) a step of preparing cDNA by using the double-stranded DNA obtained in step (c) and having a phosphorylated 5'-termini as a template, and a third primer comprising any additional nucleic acid sequence Z and said additional nucleic acid sequence Y in this order, and optionally further comprising a poly T sequence at the downstream thereof, and adding adenine (A) to the 3'-termini of the cDNA, (e) a step of linking a double-stranded DNA containing any sequence V having 3'-overhang thymine (T) to the double-stranded DNA obtained in step (d), and (f) a step of amplifying the double-stranded DNA by using the double-stranded DNA obtained in step (e) as a template, a fourth primer comprising the sequence V, and a fifth primer comprising the additional nucleic acid sequence Z, and optionally further comprising the additional nucleic acid sequence Y downstream thereof, thereby selectively amplifying a fragment of the double stranded DNA comprising the 3'-terminus of the sense strand of the cDNA generated in step (b).

2. The method according to claim 1, wherein the double-stranded DNA used in step (a) is prepared by a method containing the following steps:

(i) a step of preparing a primary stranded cDNA by reverse transcription using an mRNA isolated from a biological sample as a template, and a sixth primer composed of the additional nucleic acid sequence Y and the poly T sequence, (ii) a step of preparing a double-stranded DNA, which is a secondary strand, including subjecting the primary stranded cDNA obtained in step (i) to a poly A tailing reaction, and using the primary stranded cDNA as a template, and a seventh primer composed of the additional nucleic acid sequence X and the poly T sequence, and (iii) a step of amplifying the double-stranded DNA obtained in step (ii) by using an eighth primer comprising the additional nucleic acid sequence X, and optionally further comprising a poly T sequence at the downstream thereof, and a ninth primer comprising the additional nucleic acid sequence Y, and optionally further comprising a poly T sequence at the downstream thereof.

3. The method according to claim 1, wherein the fragmenting in step (b) is performed by sonication.

4. The method according to claim 1, wherein smoothing of the termini is performed simultaneously with phosphorylation of the 5'-termini in step (c).

5. The method according to claim 1, wherein step (c) further comprises a step of selecting a fragmented double-stranded DNA with a size of 200 bases to 250 bases.

6. The method according to claim 1, wherein the amplification in step (a) is performed by 2 to 8 cycles of PCR.

7. The method according to claim 1, wherein the amplification in step (f) is performed by 5 to 20 cycles of PCR.

8. The method according to claim 2, wherein the amplification in step (iii) is performed by 5 to 30 cycles of PCR.

9. The method according to claim 1, wherein the fifth primer used in step (f) further comprises a barcode sequence.

10. The method according to claim 1, wherein the biological sample is one to several cells.

11. The method according to claim 10, wherein the biological sample is one cell.

12. A method of measuring an amount of mRNA in cells for preparing a nucleic acid population, comprising measuring, by a next-generation sequencer, the amount of the amplified double-stranded DNA in the nucleic acid population prepared by the method according to claim 1.

* * * * *